United States Patent
Gibson et al.

(10) Patent No.: US 7,186,236 B2
(45) Date of Patent: Mar. 6, 2007

(54) INFUSION DEVICE AND INLET STRUCTURE FOR SAME

(75) Inventors: Scott R. Gibson, Granada Hills, CA (US); William A. Brandt, Castaic, CA (US); Benjamin Shen, Monterey Park, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 784 days.

(21) Appl. No.: 10/034,628

(22) Filed: Dec. 27, 2001

(65) Prior Publication Data

US 2003/0050626 A1    Mar. 13, 2003

Related U.S. Application Data

(60) Provisional application No. 60/318,056, filed on Sep. 7, 2001.

(51) Int. Cl.
*A61M 31/00*  (2006.01)

(52) U.S. Cl. .................................... 604/93.01

(58) Field of Classification Search .............. 604/6.1, 604/9, 34, 27, 30, 99.02, 99.03, 99.04, 167.03, 604/167.04, 167.05, 236, 237, 247, 288.03, 604/288.02, 323, 288.01, 335, 288.04, 93.01, 604/95.02

See application file for complete search history.

(56) References Cited

U.S. PATENT DOCUMENTS

| | | | |
|---|---|---|---|
| 4,193,397 A | 3/1980 | Tucker et al. | |
| 4,468,221 A | 8/1984 | Mayfield | |
| 4,573,994 A | 3/1986 | Fischell et al. | |
| 4,697,622 A | 10/1987 | Swift et al. | |
| 4,772,263 A | 9/1988 | Dorman et al. | |
| 5,167,633 A | 12/1992 | Mann et al. | |
| 5,176,644 A | 1/1993 | Srisathapat et al. | |
| 5,328,465 A | 7/1994 | Kratoska et al. | |
| 5,514,103 A | 5/1996 | Srisathapat et al. | |
| 5,527,307 A | 6/1996 | Srisathapat et al. | |
| 6,193,477 B1 | 2/2001 | Falk et al. | |

OTHER PUBLICATIONS

PCT International Search Report as issued in International Application No. PCT/US02/28282, Mailing date Dec. 12, 2002.

*Primary Examiner*—Manuel Mendez
(74) *Attorney, Agent, or Firm*—Foley & Lardner LLP

(57) ABSTRACT

An infusion device includes a disc-shaped housing that is made from a biocompatible material. The housing contains a reservoir for holding a volume of infusion medium, such as a medication to be administered to the patient. The inlet structure is coupled in flow communication with the reservoir, to allow the reservoir to be filled or re-filled. The housing has an outlet through which the infusion medium may be expelled. Any one or combination of aspects may be employed to minimize or reduce the required thickness T of the inlet structure and of the infusion device, including: the selection of a convergence angle of the cone-shaped depression to be within the range of about 60° and 180° and, preferably about 150°; a septum having one or more sealing ribs or a recess for receiving a support ring, to allow the septum to be made relatively thin without compromising sealing or support functions; a cup member having grooves and indentations formed in its inner surfaces, to improve flow of infusion medium without added structural thickness; a valve member having a relatively shallow needle-receiving depression or having a recess for receiving and sharing thickness with a the spring; and an inlet configuration which accommodates a needle having an opening located near its tip and, thus, employs a relatively short stroke of the valve member between closed and open states of the valve member.

14 Claims, 18 Drawing Sheets

INFUSION DEVICE AND INLET STRUCTURE FOR SAME

CROSS-REFERENCE TO RELATED APPLICATIONS

Embodiments of the present invention claim priority from a U.S. Provisional Application entitled "Infusion Device and Inlet Structure For Same," Ser. No. 60/318,056, filed Sep. 7, 2001, the contents of which are incorporated by reference herein.

FIELD OF THE INVENTION

The present invention relates generally to infusion devices, systems and processes and, in particular, embodiments to implantable infusion devices systems and processes employing an inlet configuration for minimizing the overall thickness dimension of the device. Further embodiments of the invention relate to inlet structures and processes of making and using such inlet structures for infusion devices and systems.

RELATED ART

Infusion devices are typically used to deliver an infusion media, such as a fluidic medication or drug, to a patient. Such medication or drug may be in the form of a liquid, gelatinous, particulate suspended in a fluid, or the like. Implantable infusion devices are designed to be implanted in a patient's body, to administer an infusion media to the patient at a regulated dosage or infusion rate.

Because implantable infusion devices are designed to be implanted in the patient's body, the dimensions of such devices can have an impact on the location in the body at which the device may be implanted, the level of comfort of the implant patient and the external appearance of the implant site. Typically, a device with relatively small dimensions and, in particular, a relatively small thickness dimension, will provide greater flexibility in the choice of location in the patient's body to place the implant and will minimize patient discomfort and minimize noticeable protrusions at the implant site. Accordingly, there is a demand in the industry for minimizing the overall dimensions, and, in particular, the thickness dimension of implantable infusion devices.

An implantable infusion device may include a generally disc-shaped housing having a diameter dimension and a thickness dimension. The housing should be sealed to inhibit unwanted leakage to or from the device, when implanted. The thickness dimension of the housing is dependent, at least in part, upon the relative placement of device components within the housing and the thickness dimensions of the device components. Such device components typically include a reservoir located within the housing for holding a volume of an infusion medium, for example, a liquid medication. Such device components also typically include a driving mechanism, such as a pump, and an electronic circuit and power source for controlling the driving mechanism. The driving mechanism may be controlled to cause the infusion medium to flow from the reservoir to the patient, through an outlet in the housing, either on a continuous basis, at scheduled or programmed times, or in response to signals from a sensor or other signal source.

Infusion devices also may include an inlet structure for receiving infusion medium into the reservoir to fill or re-fill the reservoir, for example, from a hollow needle, such as an hypodermic needle. Inlet structures have been configured with conical-shaped ports designed to receive a needle and guide the tip of the needle into an inlet opening. Such inlet structures allow an implanted infusion device to be filled or re-filled by inserting a hypodermic needle through the patient's skin at the implant site, and into the inlet port of implanted device. An infusion medium may then be dispensed from the hypodermic needle into the implanted device, or drawn from the implanted device into the needle. In this manner, the reservoir in the implanted device may be filled or refilled to increase the operational life of the implanted device. However, to effectively operate over multiple re-filling procedures, the implanted device must be capable of self sealing during and after repeated re-fill procedures.

The conical-shaped port of typical inlet structures, as well as other components of the inlet structure that provide the sealing capabilities noted above, contribute to the thickness dimension of the inlet structure and, thus, may also contribute to the overall thickness dimension of the infusion device. Accordingly, there is a further demand in the industry for an implantable device and inlet structure that not only has a minimized thickness dimension, but also has an inlet port and sealing mechanism that allows repeated re-filling and re-sealing procedures. In addition, because the length of time between re-fill operations is dependent, at least in part, on the volume capacity of the reservoir of the infusion device, there is a further demand in the industry for an implantable device having an inlet structure that does not displace volume in the reservoir section of the device.

Example implantable infusion devices are described in U.S. Pat. No. 5,514,103 and U.S. Pat. No. 5,176,644, each to Srisathapat et al. (and assigned to Minimed Technologies, Ltd.), U.S. Pat. No. 5,167,633 to Mann et al. (and assigned to Pacesetter Infusion, Ltd.), U.S. Pat. No. 4,697,622 to Swift (assigned to Parker Hannifin Corporation) and U.S. Pat. No. 4,573,994 to Fischell et al. (assigned to The Johns Hopkins University), each of which is incorporated herein by reference. Each of the above-cited patents describes an implantable infusion device which includes a generally disc-shaped housing containing a reservoir, a driving mechanism or pump, an inlet structure, an outlet and an electronic circuit for controlling the operation of the driving mechanism.

U.S. Pat. No. 4,573,994 ("the '994 patent") describes an inlet structure for an implantable infusion device, where the inlet structure includes a cone-shaped inlet port that is sealed by a septum. In one inlet example described in the '994 patent, a pressure activated valve couples the chamber below the septum to the device reservoir. Thus, an external pressure must be applied to the infusion medium received in the inlet, to allow the medium to pass the pressure operated valve. In another example described in the '994 patent, an inlet structure includes a cone-shaped inlet port and a moveable, cup-shaped poppet valve positioned below a septum. The cup-shaped poppet valve is configured deep enough to receive a length of a standard hypodermic needle, from the needle tip to a portion of the needle shaft above the opening. The depths of the cone-shaped inlet port and of the cup-shaped poppet valve contribute significantly to the thickness dimension of the inlet structure and, thus, may contribute to the thickness dimension of the overall infusion device.

U.S. Pat. No. 4,697,622 ("the '622 patent") also describes an inlet structure for an implantable infusion device, where the inlet structure includes a relatively deep, conical-shaped port or needle guide and a relatively deep poppet valve. The depth of the conical shaped port and the depth of the poppet valve both contribute significantly to the thickness dimension of the inlet structure. In addition, the inlet structure described in the '622 patent includes further components, such as an annular band and a seating ring, disposed between the septum and the poppet valve, which also contribute to the thickness dimension of the inlet structure.

Thus, notwithstanding the above example inlet structures, there remains a demand in the industry for new and improved infusion device configurations and inlet structures having reduced thickness dimensions, yet which do not compromise other operational characteristics, such as the capability to allow multiple re-fill and re-seal operations and the ease at which a re-fill operation may be carried out.

SUMMARY OF THE DISCLOSURE

The present invention relates generally to infusion devices having inlet structures. Particular embodiments relate to inlet structures for such devices and methods of making and using the same, which address one or more of the concerns and demands in the industry as noted above.

Embodiments of the present invention employ inlet structures that reduce the thickness requirements of the device, as compared to prior inlet structure configurations. In this manner, an infusion device may be formed with a relatively thin housing, without compromising the inlet operation of the device. More specifically, preferred embodiments provide an infusion device and an inlet structure for an infusion device with a relatively small thickness dimension, but without compromising sealing capabilities, fill and re-fill capabilities, and capabilities for multiple re-filling operations to improve the operational life span of the device. Various preferred embodiments are particularly suited for implant environments. Other preferred embodiments may be employed in external (non-implant) environments.

An infusion device according to an embodiment of the invention includes a generally disc-shaped housing that is made from a biocompatible or biostable material and/or coated with an appropriate biostable or biocompatible material. The housing contains a reservoir for holding a volume of medium, such as, but not limited to, a medication to be administered to the patient, a testing medium, a cleaning medium, or the like. An inlet structure is coupled in flow communication with the reservoir, to allow the reservoir to be filled or re-filled. In some embodiments, the inlet structure also may be used to remove or draw medium from the reservoir, for example to empty or flush the reservoir, or to sample or test the medium from the reservoir.

Medium may be added to or drawn from the reservoir by inserting a needle, such as an hypodermic needle, into the inlet and expelling medium from or drawing medium into the needle. In some embodiments, the reservoir is under a negative pressure relative to the pressure of in the external environment (the environment outside of the patient's epidermis). In this manner, during a fill or re-fill operation, the negative pressure within the reservoir may be used to draw or help draw infusion medium from the needle. In preferred embodiments, the negative pressure of the reservoir is sufficient to draw medium from the needle into the reservoir, without requiring an additional external force to be applied to the medium. In other embodiments, an external force, such as the force of an hypodermic needle plunger, may be imparted on medium within the needle, to convey or help convey the medium from the needle to the reservoir during a fill or re-fill operation. In further preferred embodiments, the reservoir pressure is negative relative to the implant environment (the environment within the patient's body, at the implant site), to help reduce the risk of undesired leakage of medium from the reservoir, into the surrounding implant environment.

The housing has an outlet through which the infusion medium may be expelled in a controlled fashion. The reservoir is coupled in fluid flow communication with the outlet. In some embodiments, a drive mechanism may be coupled in fluid flow communication with the reservoir, to drive infusion fluid out of the reservoir, through the outlet. In other embodiments, medium may be forced from the reservoir by a positive pressure applied to the reservoir (or a positive pressure differential between the reservoir and the outlet), in which case, delivery of medium may be controlled or limited by the outlet configuration, an outlet catheter configuration, capillary resistance or the like. Alternatively, medium may flow or be drawn from the reservoir by other suitable means.

Embodiments of the invention may employ any one or combination of aspects described herein for minimizing or reducing the required thickness dimension $T_I$ of the inlet structure and, preferably, for minimizing or reducing the contribution of the inlet structure to the overall thickness dimension T of the infusion device. In one preferred embodiment, all aspects described herein are employed to result in an inlet structure or infusion device with a relatively small thickness dimension.

According to one aspect of the invention, the inlet structure includes a cap member provided with a generally cone-shaped depression for contacting and guiding a needle into an inlet opening, during a fill or re-fill procedure. The cone-shaped depression defines an angle of convergence that is selected to be within the range of about 60° and 180° and, preferably about 150°. An angle of convergence within the above range and, preferably about 150°, provides sufficient needle guiding functions, yet does not require a depression thickness $T_D$ as large as various prior inlet configurations.

According to another aspect of the invention, the inlet structure includes a septum configured to provide sealing functions, yet without requiring a significant contribution to the overall thickness $T_I$ of the inlet structure. In preferred embodiments, the septum may have one or more sealing ribs to assist in providing sealing functions without requiring additional structural thickness. In further preferred embodiments, the septum may be made relatively thin and may be abutted against a rigid support member, such as a rigid, annular support ring, to improve the structural strength of the septum without requiring significant septum thickness $T_S$ to provide such structural strength. In yet further preferred embodiments, the septum is provided with a recess in which the support member is disposed, so that the septum shares at least a portion of the thickness dimension of the support member.

In some preferred embodiments, the septum includes a surface which forms a valve seat for a moveable valve structure, such that the septum and valve seat are provided as a single, unitary structure. In alternative preferred embodiments, a separate valve seat member is disposed within a recess provided in the septum, to minimize the overall thickness requirements of the septum and valve seat combination and/or to provide additional support for the septum.

According to a further aspect of the invention, the inlet structure includes a cup member having grooves and indentations formed in its inner surfaces, to improve flow of infusion medium without added structural thickness.

According to yet a further aspect of the invention, the inlet structure is provided with a moveable valve member having a relatively shallow depression for receiving the tip of a needle during a filling or re-filling procedure. The needle-receiving depression in the valve member may have a depth within the range of about 0.010 inch and about 0.050 inch. In preferred embodiments, the inlet structure is configured to function as a part of a system which includes a needle having a relatively short length between the needle tip and the needle opening. With the use of such a needle, the thickness dimension of the portion of the inlet structure that contains the moveable valve member may be reduced, by allowing the depth of the needle receiving depression to be reduced and/or the length of the maximum stroke of movement which the valve member must move during a fill or re-fill procedure to be reduced.

According to yet a further aspect of the invention, the inlet structure includes a septum that also functions to provide a valve seat for an inlet valve. In this manner, a separate valve seat element is not necessary and the additional complexity, cost and thickness that otherwise would have been contributed by a separate valve seat element may be avoided.

These and other aspects and advantages of the invention will be apparent to one of skill in the art from the accompanying detailed description and drawings. Each of the above-noted aspects of the invention, as well as other aspects of the invention, may be practiced separately or in various combinations.

BRIEF DESCRIPTION OF THE DRAWINGS

Referring now to the drawings in which like reference numbers represent corresponding parts throughout.

DETAILED DESCRIPTION OF PREFERRED EMBODIMENTS

This description is not to be taken in a limiting sense, but is made merely for the purpose of illustrating the general principles of example embodiments of the invention. The scope of the invention is best defined by the appended claims.

As discussed above, embodiment of the present invention relates generally to infusion devices systems and processes employing inlets, and to inlet structures for such devices and systems. Various embodiments and features described herein may be employed in implantable or external infusion devices. However, certain preferred embodiments of the invention relate to such devices and inlet structures configured with a minimized thickness dimension, for example, to minimize trauma to the implant recipient (referred to herein as the patient), to improve the flexibility in selecting implant sites and/or to improve the external appearance of the implant site. The term "patient" is intended to refer to the entity in which the implantable devices are implanted, whether or not the implant is carried out for medical purposes. Accordingly, the term "patient" is not to be construed as a reference or limitation to a medical context.

Figure 1:
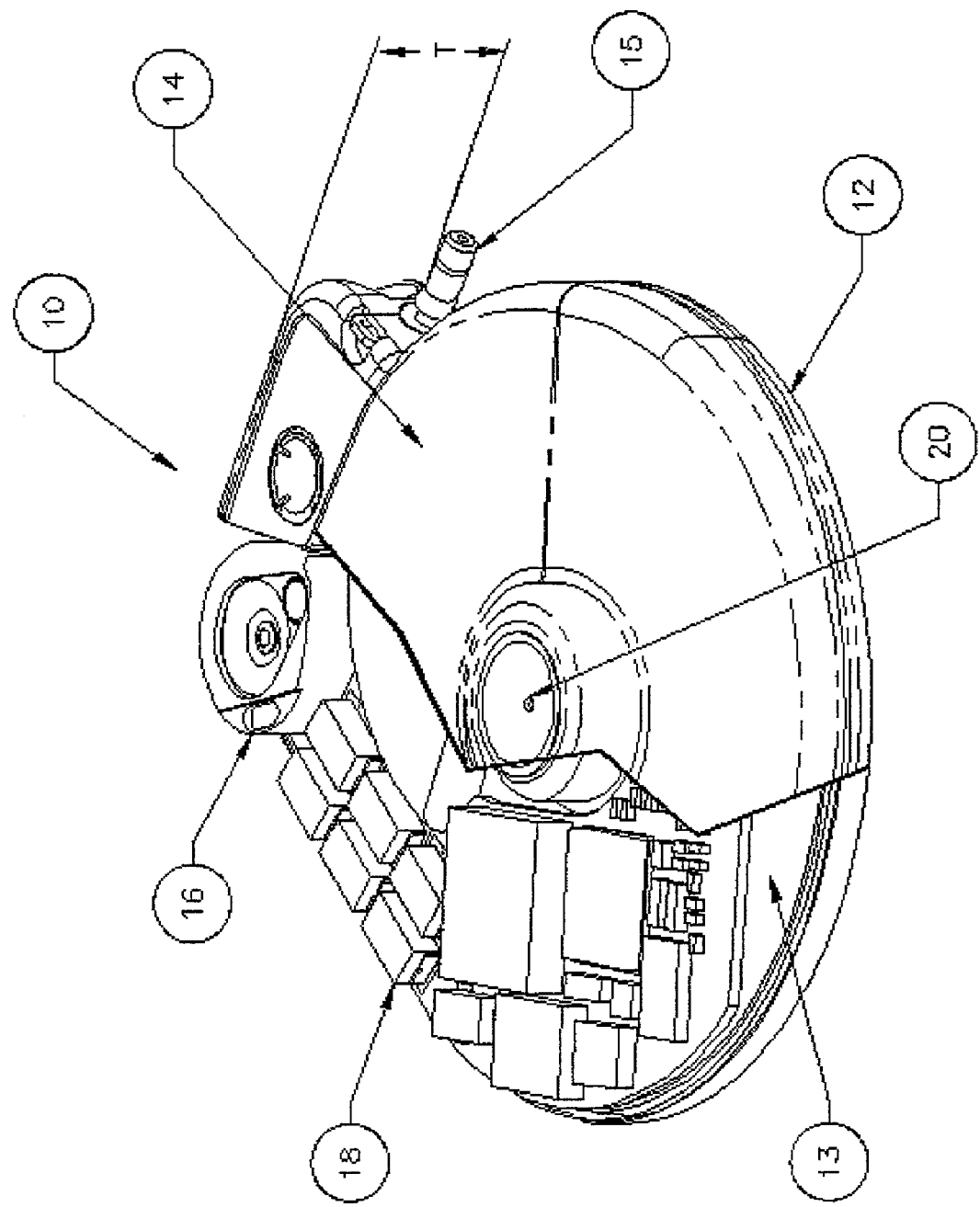
FIG. 1 is a perspective view of an implantable infusion device according to an embodiment of the invention.

FIG. 1 shows an implantable infusion device 10, according to an embodiment of the invention. The illustrated device 10 is configured to be surgically implanted into a patient. The device 10 includes a generally disc-shaped housing 12 that is made from or coated with a suitable biocompatible or biostable material. As described above, other embodiments may be employed in external (non-implant) and/or non-medical environments, where the housing 12 need not be biocompatible or biostable.

The housing 12 of the FIG. 1 has a diameter dimension D, defining the diameter of the disc shape, and a thickness dimension T, defining the overall thickness of the device. While FIG. 1 shows a circular disc-shaped embodiment, it will be understood that further embodiments of the invention may employ housings of other shapes, including, but not limited to, oval, oblong, rectangular, or other curved or polygonal shapes. Because the device is designed to be implanted in a patient's body, it is typically preferable that all edges, corners and the like be rounded or smoothed to avoid irritating tissue at the implant site. It is also typically preferable to minimize the overall dimensions of the housing 12 and, in particular, the thickness dimension T.

The housing 12 includes a reservoir housing portion 13 containing a reservoir for holding a volume of a medium, for example, but not limited to, an infusion medium such as a medication to be administered to the patient, a testing medium or a cleaning medium. The housing 12 includes a further housing portion 14, shown above the reservoir housing portion 13 in FIG. 1. Representative examples of reservoir housing portions and reservoirs which may be employed in embodiments of the invention are described in co-pending U.S. patent application Ser. No. 60/317,880, titled "Implantable Infusion Device And Reservoir For Same," which is incorporated herein by reference. However, further embodiments may employ other suitable reservoir configurations, including, but not limited to, those described in U.S. Pat. No. 5,514,103 and U.S. Pat. No. 5,176,644, each to Srisathapat et al, U.S. Pat. No. 5,167,633 to Mann et al., U.S. Pat. No. 4,697,622 to Swift and U.S. Pat. No. 4,573,994 to Fischell et al.

The housing 12 also has an outlet 15 through which the infusion medium may be expelled. When the device 10 is implanted in a patient, a catheter may be connected to the outlet 15 to deliver infusion medium expelled from the outlet 15 into the patient's blood stream or to a selected location in the patient's body. A drive mechanism 16, such as a pump, and an electronic control system 18 may be included in the portion 14 of the housing. In preferred embodiments, the drive mechanism 16 comprises a structure as described in co-pending U.S. patent application Ser. No. 60/317,886, titled "Infusion Device and Driving Mechanism For Same," filed Sep. 7, 2001 (assigned to the assignee of the present invention), which is incorporated herein by reference. The drive mechanism 16 is connected between the reservoir and the outlet 15. The electronic control system 18 includes a power source, such as a battery, and electronics for controlling the drive mechanism 16 to deliver infusion medium from the reservoir, to the patient in a selected manner, for example, according to a programmed dispensing rate or schedule.

In one embodiment, the portion 14 of the housing 12 that contains the drive mechanism 16 and control electronics 18 is hermetically sealed from the external environment and from the reservoir housing portion 13, while the reservoir housing portion 13 need not be hermetically sealed. In such an embodiment, the portion 14 of the housing containing the drive mechanism 16 and control electronics 18 may be made from titanium or titanium alloy, other metals, ceramics or other suitable biostable or biocompatible materials, while the reservoir portion 13 of the housing may be made from such materials or from a biostable or biocompatible plastic.

The infusion device 10 includes an inlet structure 20 which provides a closeable and sealable fluid flow path to the reservoir portion 13 of the housing. The inlet structure provides a port for receiving a needle through which fluid may be transferred to the infusion device, for example, to fill or re-fill the reservoir of the device. In preferred embodiments, the inlet structure is configured to re-seal after a fill or re-fill operation, and to allow multiple re-fill and re-seal operations.

As described above, the inlet structure can contribute to the overall thickness dimension T of the infusion device 10. Accordingly, preferred embodiments of the present invention relate to and employ inlet structures that reduce the thickness requirements of the device. In this manner, embodiments of the present invention may employ thinner housings, as compared to prior infusion device configurations.

The ability to reduce or minimize the device thickness dimension T, without compromising the inlet capabilities, can provide significant advantages with respect to patient comfort, appearance, flexibility in selecting implant locations on the body. Accordingly, inlet structures that allow for reduced or minimized device thickness dimensions, as described herein, may provide significant advantages in the implantable infusion device technology.

Figure 2:
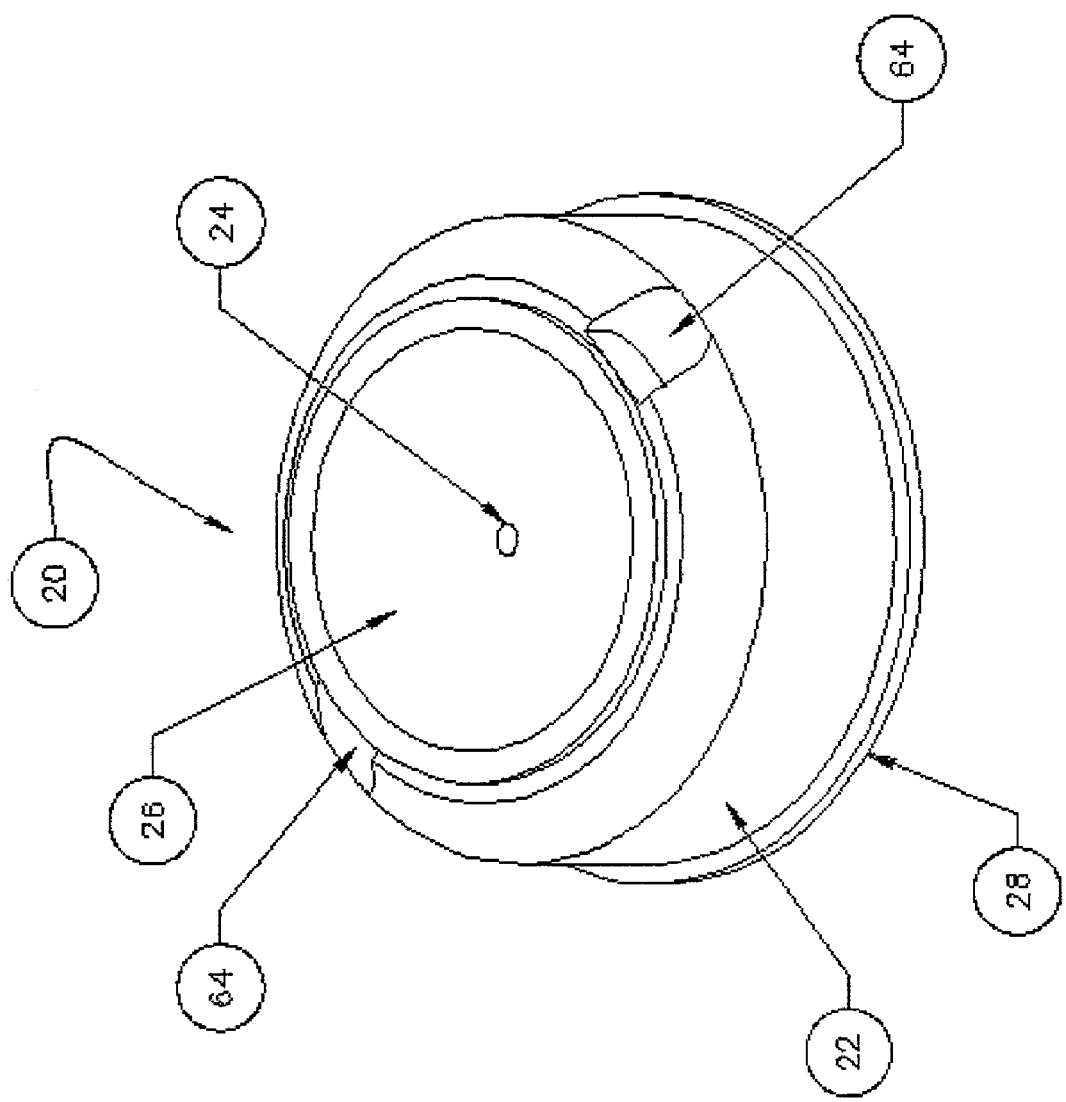
FIG. 2 is a perspective view of an inlet structure for an implantable infusion device according to an embodiment of the invention.

FIG. 2 shows an inlet structure 20 according to an embodiment of the present invention. In the illustrated embodiment, the inlet structure 20 has a generally cylindrical outer surface 22 and two ends (an upper end and a lower end when oriented as shown in FIG. 2). The upper end in FIG. 2 has an inlet opening 24 at the apex of a cone-shaped depression 26. The bottom end in FIG. 2 has a lip 28 extending outward and around the circumference of the inlet structure.

Figure 3:
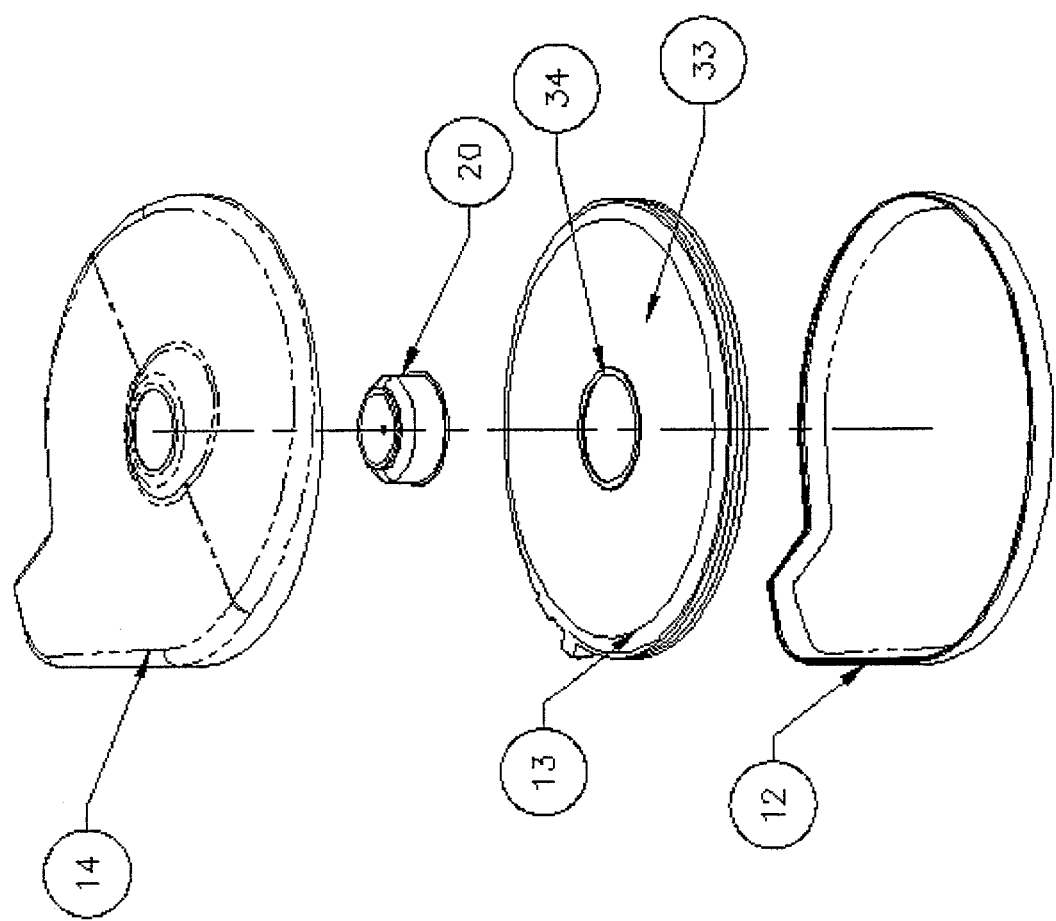
FIG. 3 is a partial exploded view of the device of FIG. 1, with the inlet structure of FIG. 2.

The inlet structure 20 of FIG. 2 may be configured to be part of an assembly of components that, when assembled, form the infusion device 10 of FIG. 1. FIG. 3 is a partially exploded view of the infusion device 10, showing the location of the inlet structure 20 within the assembly. The assembly also includes the reservoir portion 13 and the further portion 14 of the housing 12.

The reservoir housing portion 13 includes an interior 30 for containing a reservoir structure (not shown) to hold a volume of infusion medium, such as, but not limited to, medication, a testing medium, a cleaning medium or the like. The reservoir housing portion 13 also includes a cover 32 composed of a disc-shaped member having a circular, central opening 34. The opening 34 has a diameter of about, or slightly larger than, the diameter of the outer surface 22 of the inlet structure 20, but smaller than the outer diameter of the lip 28 of the inlet structure. The inlet structure 20 is configured to fit within the opening 34, as shown in FIG. 4.

Figure 4:
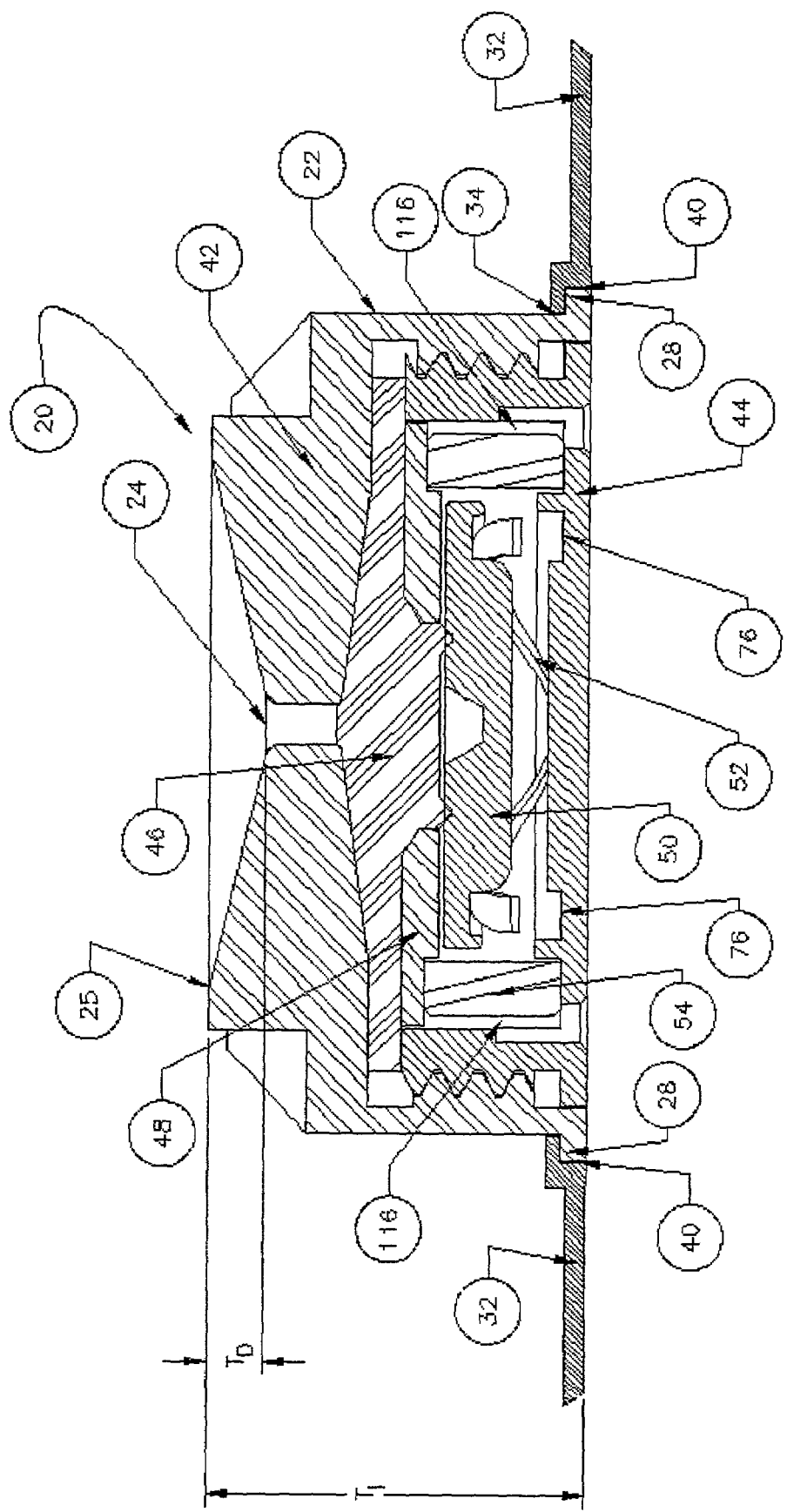
FIG. 4 is a cross-section view of the inlet structure of FIG. 2, where the valve member is in a closed state.

FIG. 4 shows a cross-section view of the inlet structure 20, assembled with the cover 32 (partially illustrated). As shown in FIG. 4, when the inlet structure 20 is assembled with the cover 32, the lip 28 of the inlet structure is located on the reservoir side of the opening 34, while the majority of the inlet structure is located on the opposite side of the opening (outside of the reservoir housing portion 13).

The reservoir side of the cover 32 may be provided with an annular recess 40, in which the lip 28 may sit. In the illustrated embodiment the recess 40 has a circumference that is slightly larger than the circumference of the lip 28 and has a depth that is slightly larger than the thickness of the lip 28, such that the lip 28 fits completely within the recess 40. As a result, the bottom end of the inlet structure 20 in FIG. 4 is generally flush with or inset from the bottom surface of the cover 32. In further embodiments, inlet 20 may be formed without lip 28 and/or cover 32 may include one or more small apertures (instead of opening 34 for allowing fluid flow between the inlet and the reservoir within the housing portion 13. In preferred embodiments, however, the inlet structure requires minimal or no space within the reservoir housing portion 13, allowing maximum use of the internal volume of the reservoir housing portion for containing infusion medium, reservoir components and, in some embodiments, a propellant medium.

Figure 5:
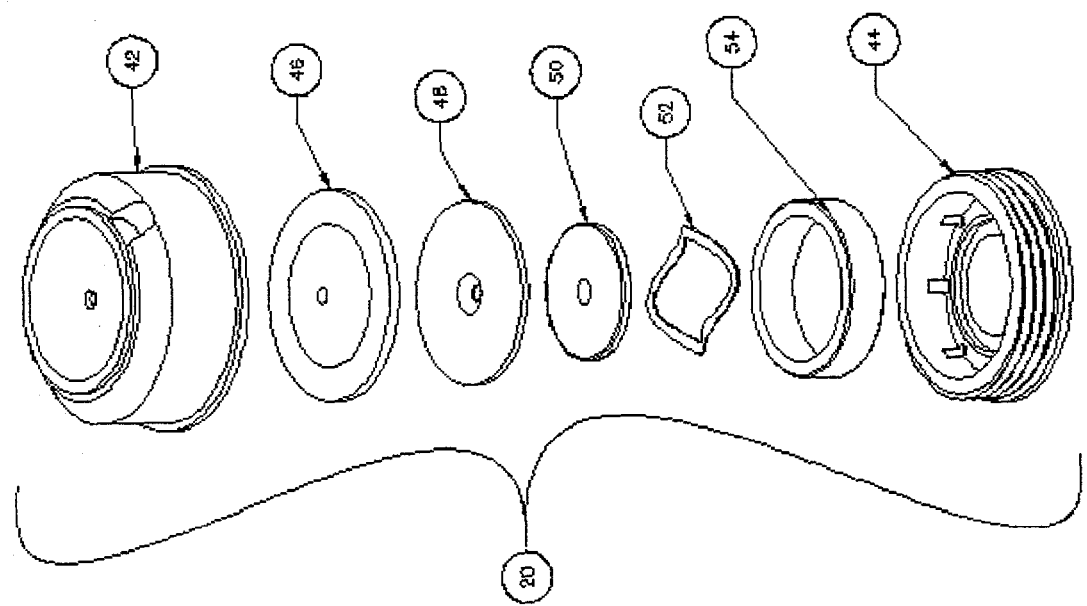
FIG. 5 is a partial exploded view of the inlet structure of FIGS. 2 and 4.

In the illustrated embodiment, the inlet structure 20 comprises an assembly of components shown in a partially exploded view in FIG. 5. With reference to FIGS. 4 and 5, the inlet structure 20 comprises an outer cap 42, a cup-shaped member 44, a septum 46, a support ring 48, a valve member 50, a spring 52, and a filter member 54.

Figure 6:
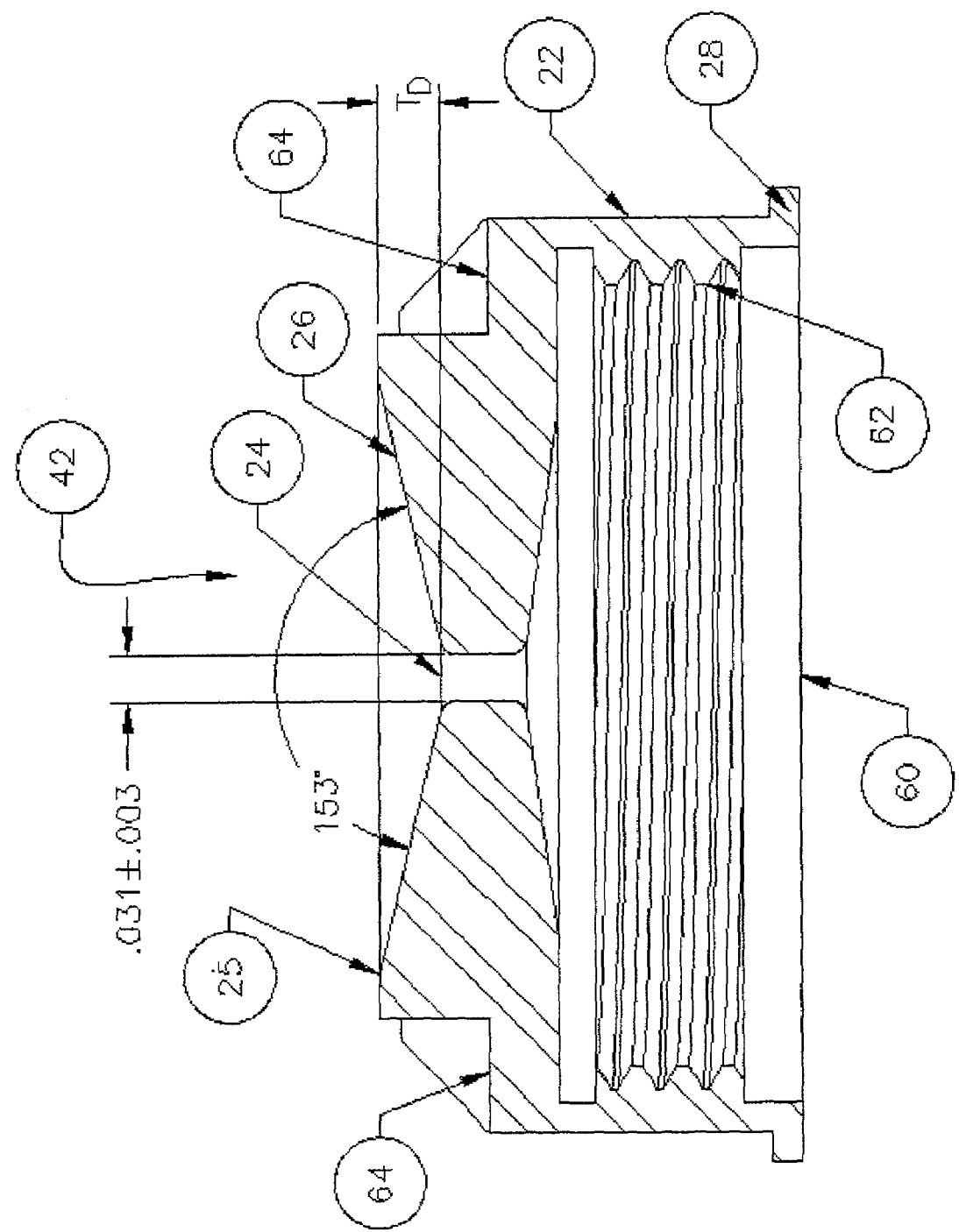
FIG. 6 is a cross-section view of an outer cap of the inlet structure of FIGS. 2 and 4.

The outer cap 42 of the inlet structure is shown in cross-section, in FIG. 6. The cap 42 may be made of or coated with any suitable biostable or biocompatible material, such as, but not limited to, titanium, titanium alloy, stainless steel, ceramic, glass, plastic, or the like. The cap 42 comprises a generally rigid cylindrical body which defines the generally cylindrical shape of the inlet structure, including the outer surface 22 and the lip 28 of the inlet structure.

The cap 42 also defines the generally cone-shaped depression 26 and the opening 24 of the inlet. In particular, the generally cone-shaped depression 26 is provided in one end of the cap 42, while the lip 28 is provided at the opposite end of the cap. The diameter of the inlet opening 24 is selected to be slightly larger than the maximum diameter of the needle used to fill or refill the reservoir. In one embodiment the diameter of the inlet opening 24 may be any diameter within the range of about 12 to about 30 gauge and, in preferred embodiments, is about 0.31 of an inch.

The shape of the depression 26 is selected to provide a needle guiding function, to help guide a needle into the inlet opening 24. In addition, the shape of the depression may be selected to reduce or minimize the overall thickness $T_I$ required by the inlet structure 20. In the illustrated embodiment, the generally cone-shaped depression 26 has a straight wall, shown as straight lines in the cross-section view of FIG. 6, which defines a cone-shape having an angle of convergence. In further embodiments, the cone-shaped depression 26 may have a curved wall, defining an angle of convergence that is different at different diameters of the depression, for example a wall defining a curve which decreases or increases in convergence angle with increasing distances from the inlet opening 24. In yet further preferred embodiments, the depression includes an abrupt drop defining an annular wall 25 at the outer perimeter of the depression, for providing a stop surface to inhibit a needle from sliding out of the depression 26, once the needle has found the depression.

As the angle of convergence of the depression 26 affects the thickness dimension $T_D$ of the depression 26, which, in turn, can contribute to the overall thickness $T_I$ of the inlet structure 20, an embodiment of the invention employs a depression 26 selected to minimize the thickness $T_D$, for example, having an angle of convergence (or an average angle of convergence) within the range of about 60° and about 180° and, preferably, about 150°. An angle of convergence within the above range and, preferably about 150°, provides sufficient needle guiding functions, yet does not require a thickness $T_D$ as large as various prior inlet configurations. In one preferred embodiment, the diameter of the depression 26 is selected to be about 0.4 inch and a straight angle of convergence is selected to be about 150°, such that the thickness $T_D$ is about 0.05 inch.

With reference to FIG. 6, the cap 42 has a hollow interior 60 and a threaded inner wall 62 surrounding the interior 60. The inlet opening 24 provides an open passage extending from the center of the depression 26, to the interior 60, through which a needle may pass, for example, during a fill or re-fill operation. The inner wall 62 is threaded to allow engagement with opposite facing threads on the outer surface of the cup member 44, when assembled as in FIG. 4. The cap 42 and the cup member 44 may be assembled together in a screw-threading manner, by engaging the threaded walls of the two components and rotating one relative to the other about the axis A (as shown in FIG. 5).

The cap 42 may be provided with a means for engaging a tool to help rotate the cap and cup member relative to each other about its axis A. In the illustrated embodiment, such tool engagement means includes a pair of indentations 64 at the outer peripheral edge of the cap end, at diametrically opposite sides of the axis A. In further embodiments, a single indentation or more than two indentations may be employed. In yet further embodiments, one or more indentations may be located in other suitable locations on the cap 42. The indentation(s) is (are) configured to engage one or more correspondingly shaped and placed tines or ribs on a rotatable tool (not shown). In yet further embodiments, an indentation forming a cross shape, star shape or slot shape may be located on the depression surface and centered relative to the axis A, for engaging a screw-driver or similar tool having a cross (for example, Phillips style), star or standard head. Similarly, in yet further embodiments, the cap 42 may be provided with one or more ribs, tines, cross, star or slot-shaped protrusions which engage one or more correspondingly shaped indentations in a rotatable tool (not shown). Once engaged, the tool may then be rotated (or held stationary while the cup member 44 is rotated) to, for example, assemble, disassemble or adjust the connection between the outer cap 42 and the cup member 44.

Figure 7:
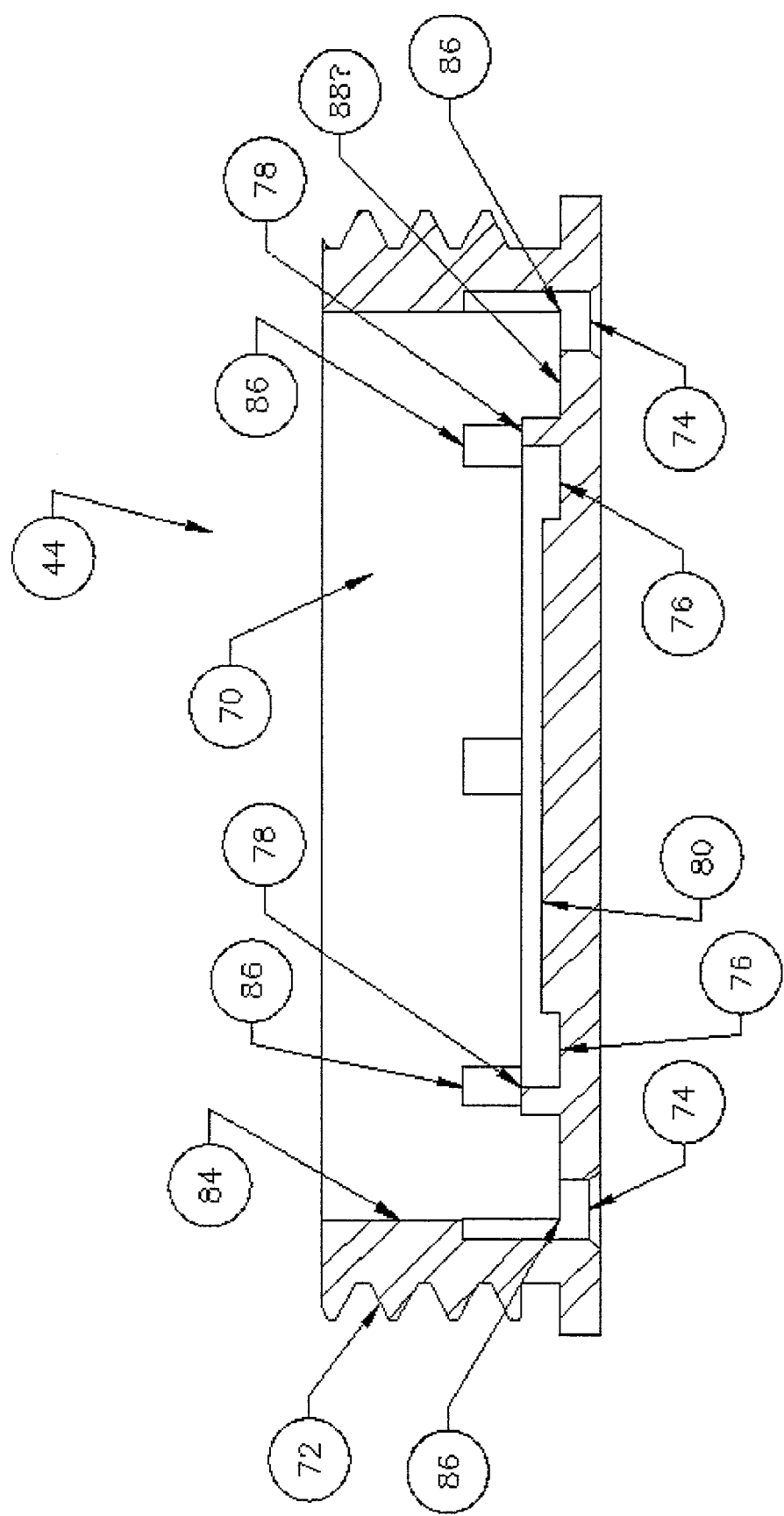
FIG. 7 is a cross-section view of a cup member of the inlet structure of FIGS. 2 and 4.
Figure 8:
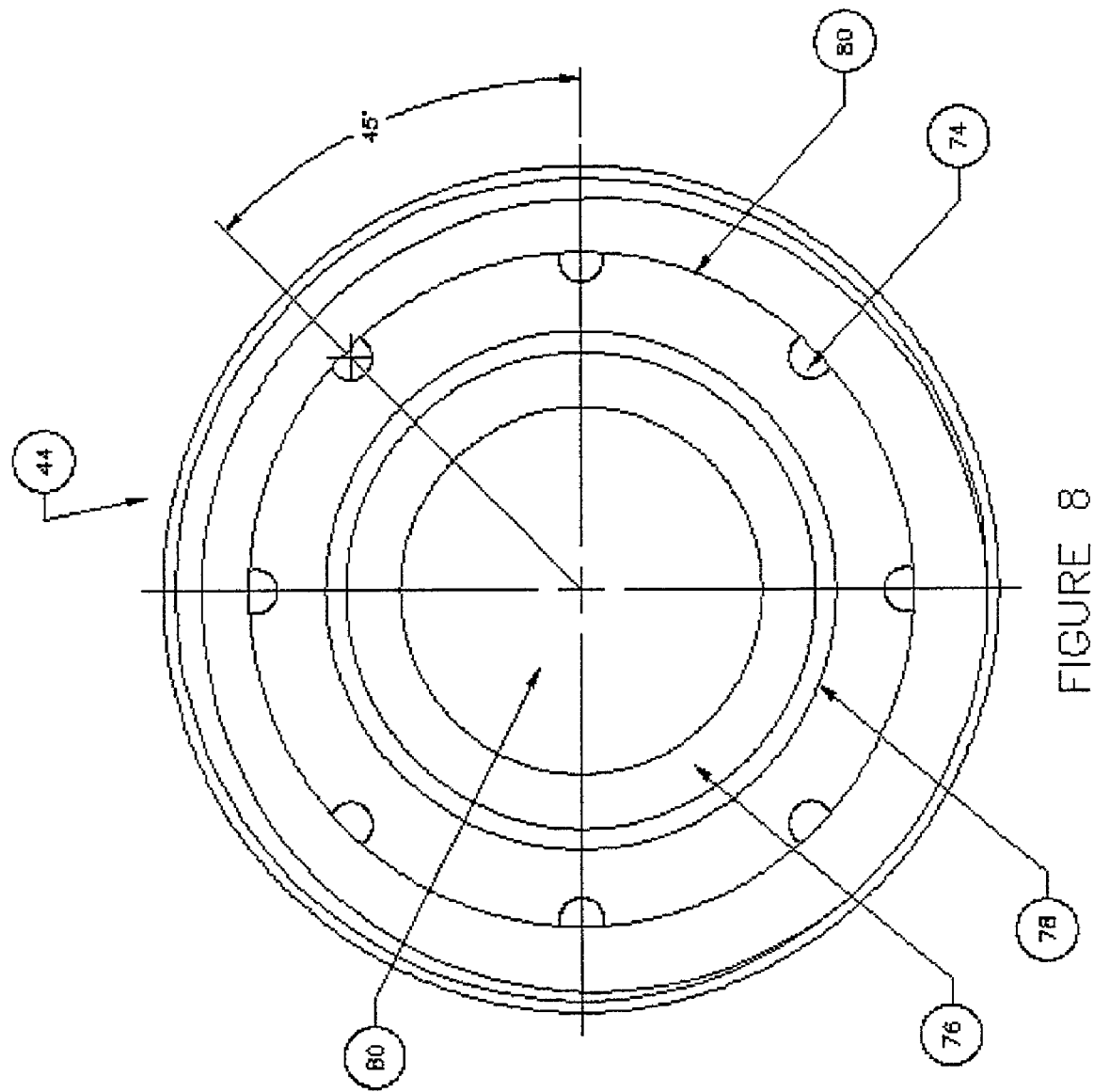
FIG. 8 is a top view of the cup member of FIGS. 2 and 4.

The cup member 44 of the inlet structure 20 is shown in cross-section in FIG. 7 and as a top view in FIG. 8. The cup member 44 may be made from or coated with any suitable infusion medium compatible material. In embodiments in which the cup member 44 may come in contact with bodily fluids or tissue, the cup member may be made of or coated with a suitable biostable or biocompatible material, such as, but not limited to, titanium, titanium alloy, stainless steel, ceramic, glass, plastic or the like. The cup member 44 comprises a generally rigid cup-shaped body, having a generally hollow interior 70 and a threaded outer surface 72. The threaded outer surface is configured to engage the threaded inner wall 62 of the cap 42, as described above. The interior surface of the end of the cup member 44 includes a number of apertures 74, an annular groove 76, an annular raised portion 78 around the groove 76 and a central portion 80 surrounded by the annular groove 76.

The apertures 74 provide a passage through which infusion medium or other material from a needle may pass through the inlet structure 20, to fill or re-fill the reservoir of infusion device 10 (FIGS. 1 and 3). In some embodiments, the apertures 74 also allow communication of medium out from the reservoir, through the inlet structure 20, for example, to empty or flush the reservoir. In the illustrated embodiment, cup member 44 has eight, evenly spaced apertures 74, each at 45° angles relative to adjacent apertures. However, other embodiments may employ any suitable number of apertures greater or fewer than the eight, in any suitable pattern, including a single aperture pattern. However, multiple apertures in an evenly spaced pattern are preferred, to provide suitable flow volume for more quickly transferring infusion medium and minimizing locations within the cup member in which infusion medium may be trapped. An evenly spaced pattern of apertures 74 may also help to more uniformly burden the filter element 54, described below.

The apertures 74 may be connected by one or more grooves, such as annular groove 82 (shown in FIG. 8), to form one or more channels connecting the apertures. The annular channel formed by the groove 82 improves distribution and flow of infusion medium to the apertures 74. In the illustrated embodiment, the apertures 74 are located adjacent the inner wall 84 of the cup member 44. The inner wall 84 may also include an indentation 86 adjacent each aperture 74, in fluid flow communication with the adjacent aperture 74, to further improve the flow efficiency of the structure.

When the inlet structure 20 is assembled as shown in FIG. 4, the raised portion 78 provides an annular surface which abuts the inner peripheral surface of the filter member 54. An annular surface 88 surrounds the raised portion 78, for abutting one end of the filter member 54. The groove 76 contains and retains a portion of the spring 52 and the central portion 80 has a surface facing the valve member 50. In one embodiment, the valve-facing surface of the central portion 80 provides a stop member for contacting and stopping the movement of the valve member 50 at the end of its open stroke. In other embodiments, the tension of the spring 52 is selected to be great enough to inhibit contact between the valve member 50 and the surface of the central portion 80 during normal fill or re-fill operations, for example, to minimize damage to any infusion media that may be in the space between the central portion 80 and the valve member 50.

Figure 9:
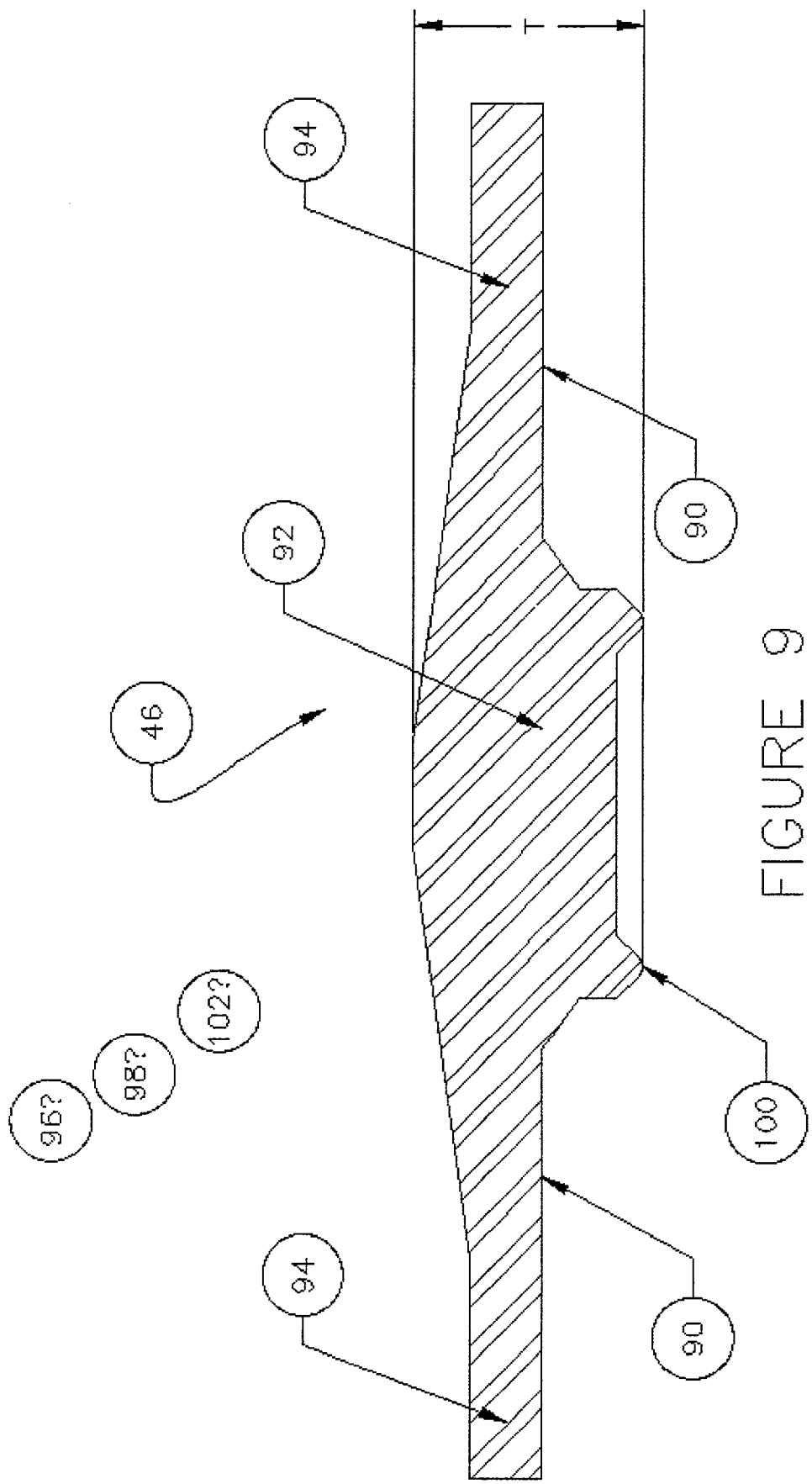
FIG. 9 is a cross-section view of a septum of the inlet structure of FIGS. 2 and 4.

The septum 46 is shown in cross-section in FIG. 9. The septum may be composed of any suitable biostable or biocompatible and infusion medium compatible material capable of being pierced by a needle, forming a seal around the needle during a fill or re-fill operation, and resealing after removal of the needle. Suitable septum material may include, but is not limited to polymers such as silicon rubber, ethylane propylene, neoprene, latex, Teflon, or the like. The septum may be provided with a centrally located slit (not shown), for assisting the passage of the needle through the septum material.

With reference to FIGS. 5 and 9, the septum 46 comprises a round, disc-shaped member that has an annular recess 90 around its periphery. The annular recess 90 defines a central portion 92 which is thicker than the peripheral portion 94 of the septum. The thickness $T_S$ at the central portion 92 of the septum is selected to provide a suitable seal against a needle passing through the septum during access operations (such as a fill, re-fill or fluid withdrawal operations) and a re-seal after removal of the needle, preferably, a specified minimum number of repeated times.

The support ring 48 is configured to fit within the annular recess 90 of the septum 46, as shown in FIG. 4. The support ring 48 may be made of or coated with any suitably rigid, infusion medium compatible material such as, but not limited to, titanium, titanium alloy, stainless steel, ceramic, glass, polymer or the like. When located within the recess 90, the support ring 48 provides structural support and rigidity to the septum 46. In this manner, the septum 46 may be made with a relatively small overall thickness $T_S$, without compromising structural rigidity. In other words, the thickness $T_S$ of the septum need not be increased beyond the thickness needed to provide the sealing function described above. Accordingly, the contribution of the septum thickness $T_S$ to the overall thickness T of the inlet structure may be minimized.

In the illustrated embodiment, the support ring 48 and the annular recess 90 are dimensioned such that the support ring fits completely within the recess 90. In this manner, the thickness $T_S$ of the central portion 92 of the septum defines the overall septum thickness. In other embodiments, the support ring 48 may extend beyond the thickness of the central portion 92, when placed in the recess 90.

The septum 46 may be provided with annular ribs 96, 98 and 100, and one or more peripheral ribs 102 for assisting in the sealing function of the septum. When assembled as shown in FIG. 4, the annular rib 96 may engage and be received within a corresponding annular groove in the inner surface of the end of the cap 42. In yet alternative embodiments, the inner surface of the end of the cap 42 may be provided with an annular protrusion for engaging and deforming a portion of the septum 46 or being received within a corresponding, annular groove in the septum 46.

The annular rib 98 is positioned to engage the support ring 48, to improve the seal between the septum 46 and the support ring 48. The annular rib 100 is positioned to engage the valve member 50, when the valve is closed, to improve the seal between the septum 46 and the closed valve member 50. The peripheral rib 102 may be positioned to engage and be received within a corresponding annular groove 108 in the inner wall 84 of the cup member 44. In yet alternative embodiments, the inner wall 84 of the cup member 44 may be provided with an annular protrusion for engaging and deforming a portion of the peripheral edge of the septum 46 or being received within a corresponding, annular groove in the peripheral edge of the septum 46.

In further embodiments, the ribs 96–102 may engage generally smooth surfaces of the cap 42, cup member 44 and valve member 50, instead of engaging correspondingly shaped grooves in those surfaces. In such embodiments, the ribs 96–102 may be forced against the generally smooth surfaces and partially deform against those surfaces to improve the seal between the septum and those surfaces.

Thus, in the above-described embodiments, the annular and peripheral ribs 96–102 improve the sealing function of the septum 46, without significantly increasing the overall thickness $T_S$ of the septum. Moreover, the peripheral rib 102 improves the seal of the septum against cup member 44, without requiring a thicker peripheral septum edge and, thus a wider septum thickness $T_S$ for increased sealing surface area contact. Accordingly, the annular and peripheral ribs provide yet a further mechanism for minimizing or reducing the contribution of the septum thickness $T_S$ to the overall thickness T of the inlet structure 20.

Figure 10:
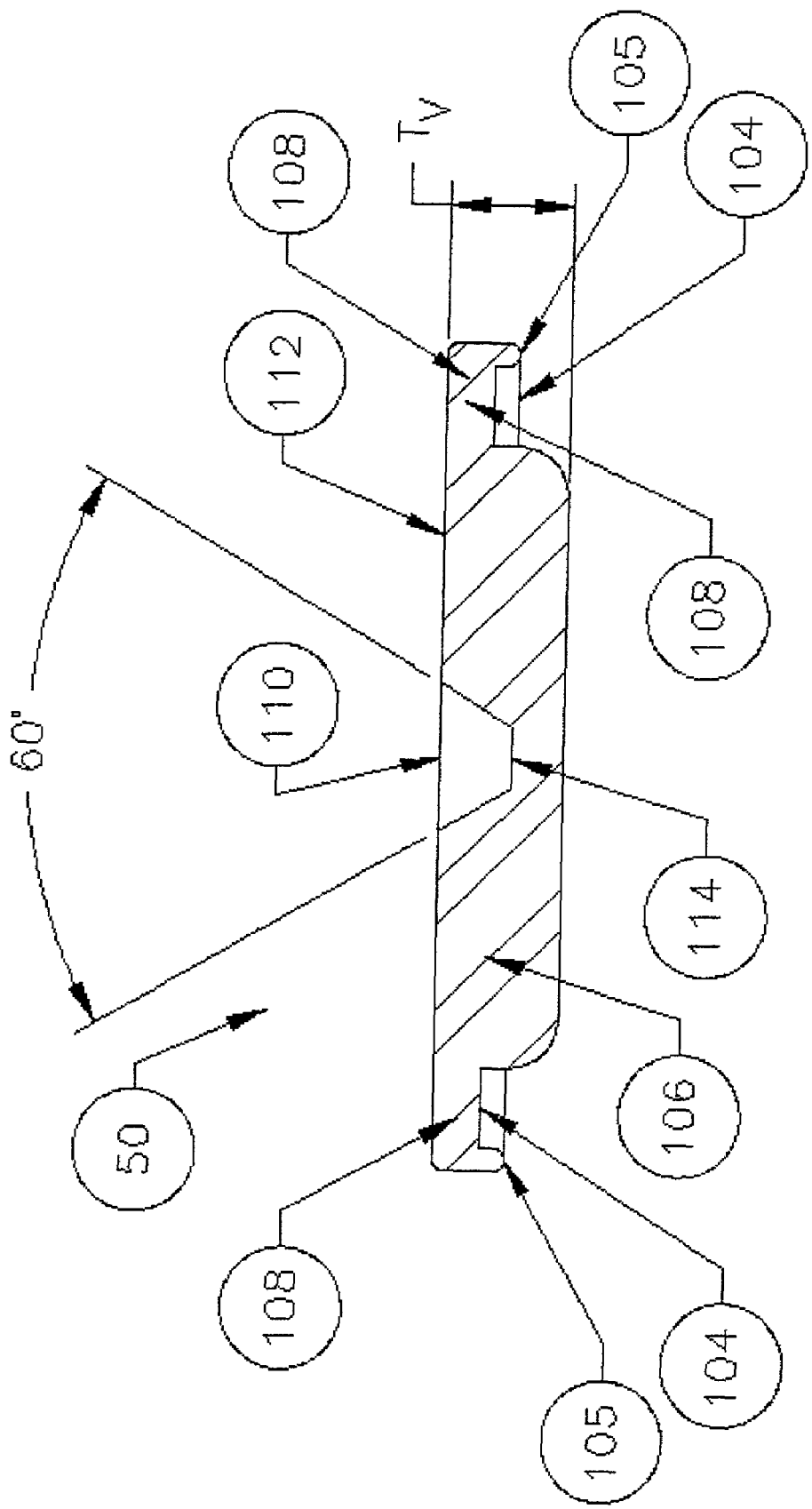
FIG. 10 is a cross-section view of a valve member of the inlet structure of FIGS. 2 and 4.

The valve member 50 is shown in cross-section in FIG. 10. The valve member 50 may be made of or coated with any suitable infusion medium compatible material such as, but not limited to, titanium, titanium alloy, stainless steel, ceramic, glass, polymer, or the like. With reference to FIGS. 5 and 10, the valve member 50 has a generally rigid, circular disc-shaped body, with an annular recess 104 around the peripheral edge of one side face of the body. The recess 104 defines a central portion 106 which is thicker than the peripheral portion 108 of the valve member.

A depression 110 is provided in the opposite side face of the valve member body, relative to the face having the annular recess 104. The depression side of the valve member body has an annular surface 112 around the depression. The depression 110 provides a seat for a needle that has passed through the septum, for example, during a fill, re-fill or fluid withdrawal operation. In the illustrated embodiment, the depression 110 has a generally frusto-conical shape, which converges inward toward a flat base 114.

Preferably, the angle of convergence of the depression 110 is small enough and/or the diameter of the base 114 is large enough to allow the needle to easily find the depression upon passing through the septum. The diameter of the depression 110 should also be large enough to provide a sufficient gap between the opening in a needle seated within the depression and the body of the valve member, to allow infusion medium to flow from the needle with little or no obstruction from the valve member body. However, the diameter of the depression 110 should not be so large as to result in insufficient support of the septum against the downward (with respect to the illustrated orientation) force applied by a needle being pushed through the septum 46.

In preferred embodiments, the angle of convergence may be within the range of about 30° and about 150° and the diameter of the base 114 may be within the range of about 0.125 inch and about 0.5 inch. In the illustrated embodiment, the angle of convergence of the depression 110 is about 60° and the diameter of the base is about 0.025 inch. The depression 110 is configured to receive a tip of a needle, as described below with respect to FIG. 12.

The annular recess 104 in the valve member body is configured to receive a portion of the spring 52, when the inlet structure is assembled as shown in FIG. 4. The valve member 50 may include an annular rib 105 at the outer periphery of the annular recess 104, to help retain the spring 52 within the recess 104. With the spring seated within the recess 104, a portion of the thickness dimension of the spring is shared by a portion of the thickness dimension of the valve member body, such that the contribution of the spring and valve member to the overall thickness T of the inlet structure is less than the sum of the thickness dimensions of the spring and the valve member.

With reference to FIG. 4, when assembled, the spring 52 is located between the valve member 50 and the interior surface of the bottom of the cup member 44, and is seated within the annular recess 104 in the valve member 50 and the annular groove 76 in the cup member 44. The annular recess 104 and annular groove 76 help retain the spring in a centered relation, relative to the valve member 50. The spring is tensioned to provide a spring force between the valve member 50 and the cup member 44, to force the valve member away from the cup member 44, in the direction toward the septum 46. In preferred embodiments, the spring force is sufficient to force the surface 112 of the valve member 50 against the septum 46, when the inlet structure valve is in a closed state. As described above, the rib 100 on the septum 46 is positioned to improve a seal between the septum 46 and the surface 112 of the valve member 50, when the valve member is in the closed state by the force of the spring 52 against the septum.

The spring 52 may be made of or coated with any suitable infusion medium compatible material and may have any suitable structure that is compressible and provides a restoring force. In preferred embodiments, the spring is selected to provide sufficient spring force to seal the valve member 50 against the septum 46, when in a closed state as shown in FIG. 4, yet also allow a needle to move the valve member 50 to an open state allowing adequate flow during a fill, re-fill or withdrawal operation. In addition, the type of spring 46 is preferably selected to minimize the contribution of the spring to the overall thickness T of the inlet structure. Thus, a spring having a relatively low thickness profile is preferred.

In the illustrated embodiment, the spring 52 comprises a wave compression spring, which provides a suitable spring force and is compressible to provide a sufficient amount of movement of the valve member to allow the valve member to seal in a closed position and move to an open position during a fill, re-fill or withdrawal operation. Other embodiments may employ other suitable springs, preferably of the low-profile type, including, but not limited to belville, crescent, disc, or conical coil springs. The spring may be made of materials such as, but not limited to, titanium, titanium alloy, stainless steel, MP35-N, or the like. In other embodiments, other forms of restoring means for restoring the valve member 50 to its closed position may be employed, including, but not limited to a resilient material such as foam rubber, bellows, dome switch-like mechanism, or balloon, or an electromagnet, magnet, pneumatic pressure or the like, located between the valve member and the cup member or other suitable locations.

The filter member 54 is configured to surround the valve member 50 and spring 52, when assembled as shown in FIG. 4. With reference to FIGS. 4 and 5, the illustrated embodiment of the filter member 54 is configured as an annular ring having an open interior. The filter member 54 may be made of or coated with any suitable infusion medium compatible filter material, which allows infusion medium to pass there through, including, but not limited to, porous titanium, porous ceramic, PFA, FEP, PTFE, polytetrafluoroethylene, Teflon, Gortex, other polymers, polysufone, or woven material, perforated material or the like. In preferred embodiments, the filter member 54 is suitably rigid and maintains a spacing between the septum 46 (with the support ring 48) and the bottom surface of the cup member 44, to allow the valve member 50 sufficient room to move between closed and open positions.

The filter member 54 is positioned to abut the annular raised portion 78, along the inner peripheral surface of the filter member, when assembled as shown in FIG. 4. In this manner, the annular raised portion 78 inhibits the filter member 54 from moving laterally, toward the inner wall 84 of the cup member 44. Preferably, a spacing is maintained between the filter element 54 and the inner wall 84, to facilitate the flow of infusion medium toward the apertures 74 in the cup member 44. In the illustrated embodiment, the spacing between the filter element 54 and the inner wall 84 is shown as an annular volume 116 surrounding the filter element in FIG. 4. The annular volume 116 is in flow communication with the annular groove 80, the apertures 74 and the indentations 86 in the cup member 44.

In further embodiments, the filter member 54 may be omitted or replaced with a structural support for supporting the septum 46 at a specified distance from the end of the cup member 44 but allowing passage of infusion medium toward the apertures 74. In such embodiments, a filter (not shown) may be included in or adjacent the apertures 74 or within the reservoir housing portion 13 or other portion of the infusion system.

With reference to FIGS. 4 and 5, the illustrated inlet structure may be constructed by forming components as described above in accordance with any suitable manufacturing process or processes, including, but not limited to molding, extruding, machining, a combination of such processes, or the like. Once the components are formed or obtained, the filter member 54 may be placed within the cup member 44, on the surface 88. Also, the spring 52 may be seated within the recess 104 of the valve member 50 and also within the groove 76 in the cup member 44. The support ring 48 may be seated within the recess 90 of the septum 46 and placed adjacent the filter member 54, with the annular rib 100 of the septum abutting the surface 112 of the valve member 50.

The outer cap 42 may then be threaded over the cup member 44, by engaging the threaded wall 62 of the cap 42 with the threaded outer surface of the cup member and rotating the components relative to each other. A tool may be engaged with the indentations 64 (or protrusions), to assist in the rotating operation, as described above. By so threading the outer cap 42 onto the cup member 44, the inner surface of the end of the cap 42 is forced against the rib 96 of the septum 46, to help seal the septum against the cap 42 and to retain the septum within the cup member 44, against the force of the spring 52. According to an example embodiment, adjustments of the force applied by the cap 42 against the septum 46 may be made by further threading or unthreading (tightening or loosening) the cap 42 relative to the cup member 44. Such adjustments, in turn, provide the ability to adjust and test valve performance characteristics during manufacture. In preferred embodiments, once the desired performance characteristics are selected by selectively tightening or loosening the cap 42, the cap is welded to the cup member 44, for example, as part of the manufacturing process. In alternative embodiments, the cap 42 and the cup member 44 may remain non-permanently coupled, to allow post-manufacture adjustment.

In operation, the illustrated inlet structure is configured to provide a closed state, in which the inlet is sealed against fluid flow (either inward or outward), and an open state, in which the inlet structure receives a needle and allows the fluid to pass through the apertures 74 either to or from the needle. In FIG. 4, the inlet structure is shown in a closed state, wherein two sealing mechanisms (i.e., the septum and the valve) operate to inhibit fluid flow through the structure. In alternative embodiments, either one of the two sealing mechanisms may be employed, without the other. In yet further alternative embodiments, more than two sealing mechanisms are employed.

In the FIG. 4 embodiment, the first sealing mechanism is provided by the solid (or sealed slit) nature of the septum 46 and the seal provided by the septum 46 against the end of the cap 42 and the inner wall 84 of the cup member 44. As described above, the sealing mechanism may be improved, allowing the thickness $T_S$ of the septum to be minimized or reduced, by employing ribs 96 and 102. The second sealing mechanism is provided by the valve member 50, which is forced by the spring 52 against the septum 46. As described above, the sealing mechanism provided by the valve-to-septum abutment may be improved by employing one or more ribs 100 on the surface of the septum, each of which abuts the valve member 50. Thus, in the closed state as shown in FIG. 4, the inlet structure may provide a reliable seal against fluid flow through the structure, to help seal against unwanted fluid flow into or out of the infusion device 10 (FIG. 1). In addition, the sealing mechanisms are constructed with components configured to minimize the overall thickness T of the inlet structure, without compromising sealing functions.

During a fill, re-fill or withdrawal operation, a hollow needle, such as an hypodermic needle, thin catheter or other thin-tube structure, is inserted into the inlet structure, through the inlet opening 24. In embodiments in which the infusion device 10 (FIG. 1) is implanted in a patient's body, the needle may be inserted through the patient's skin, at the implant site, to engage the depression 26 in the inlet structure. The needle may be guided by the angle or curvature of the depression 26 into the inlet opening 24 and, then, into the septum 50.

Figure 11:
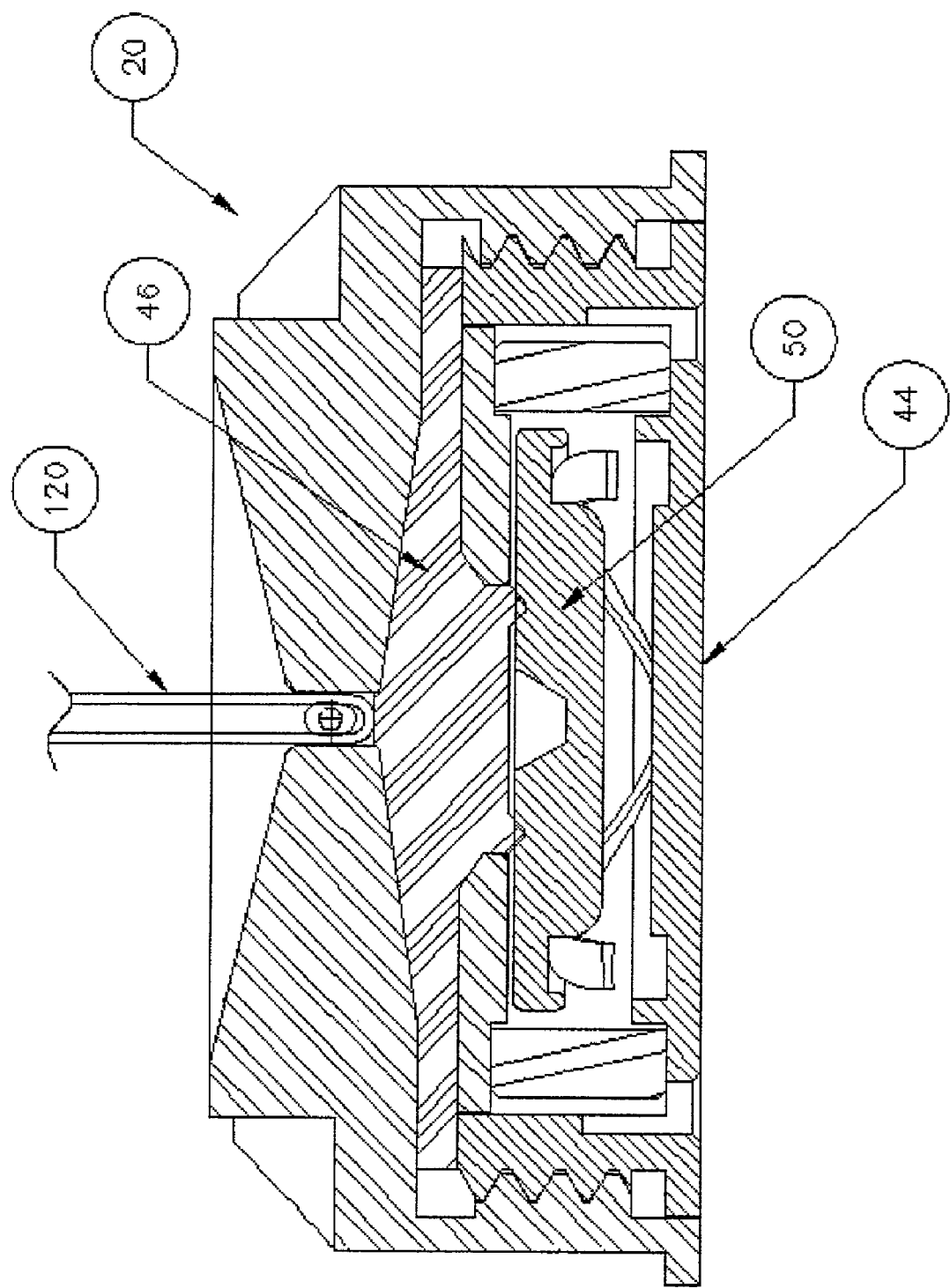
FIG. 11 is a cross-section view of a portion of the inlet structure of FIG. 2, with a needle entering the inlet opening and the valve member in a closed state.

FIG. 11 shows a needle 120 that has entered the inlet opening 24 and is beginning to pierce the septum 46. The septum 46 may be provided with a slit, either fully or partially through the body of the septum, to assist the piercing operation. Alternatively, an unslitted septum may be used with a non-coring needle. As shown in FIG. 11, the needle has not passed through the septum and, as a result, the valve member 50 remains in the closed state, in which it is forced against the septum by the spring 52.

Figure 12:
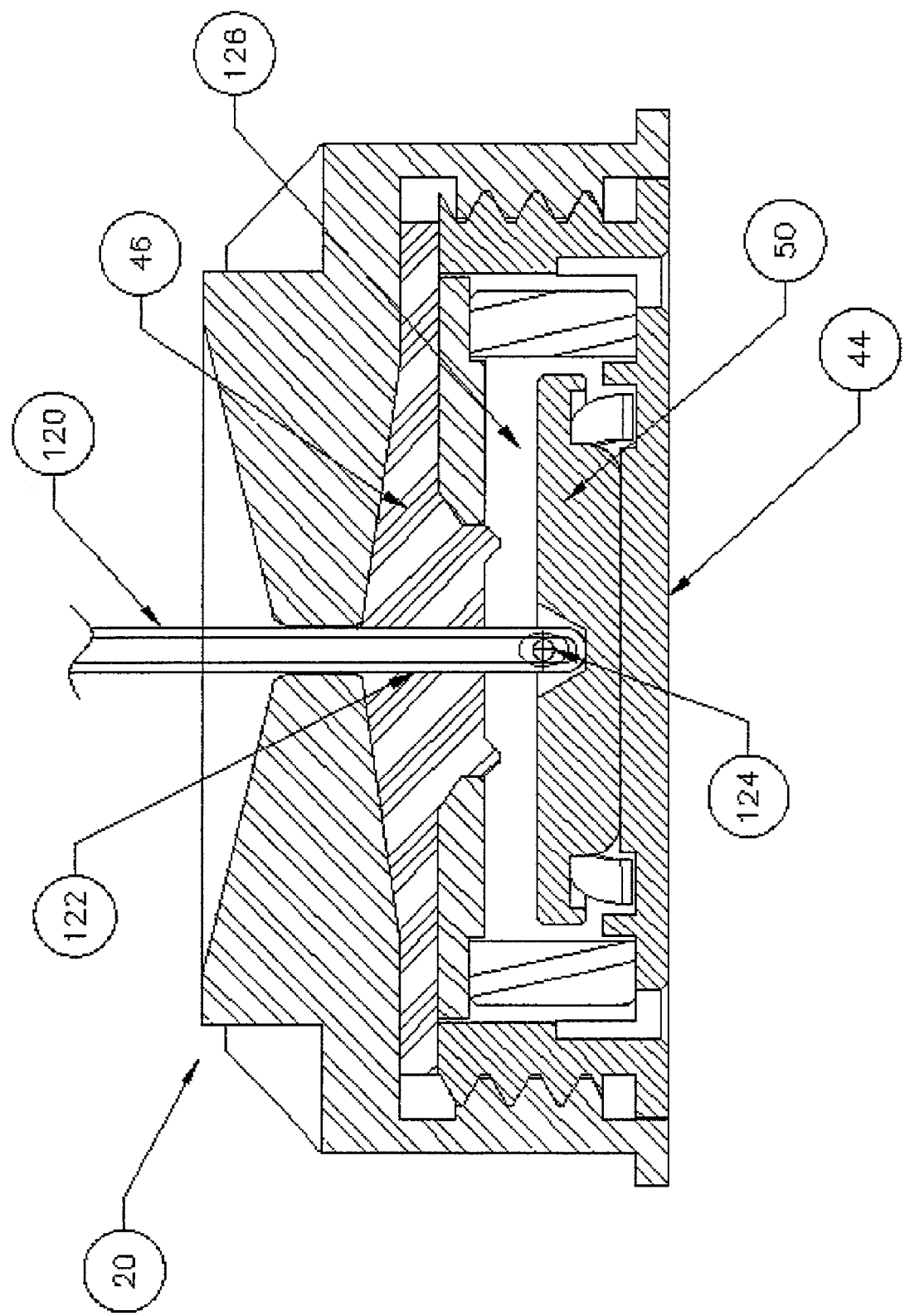
FIG. 12 is a cross-section view of a portion of the inlet structure of FIG. 2, with a needle passed through the septum and the valve member moved to an open state.

FIG. 12 shows the needle 120, after it has passed through the septum 46 and has contacted the valve member 50 and forced the valve member to move toward the end of the cup member 44, against the force of the spring 52. In the state shown in FIG. 12, the inlet structure is open to receive fluid, such as infusion medium, from the needle 120. However, the inlet structure preferably remains sealed from the external environment, by the seal formed between the needle 120 and the septum 46 at the interface 122. In this regard, the septum 46 is preferably formed of a material, as described above, that will resiliently mold around the needle 120 and, more preferably, will do so even after repeated needle insertions.

By passing the needle 120 through the septum and forcing the valve member 50 into an open state, as shown in FIG. 12, fluid may be expelled or drawn out from an opening 124 in the needle. In some embodiments, the interior of the reservoir may be under a negative pressure relative to the pressure of in the external environment (e.g., the environment outside of the patient's epidermis). In this manner, during a fill or re-fill operation, the negative pressure within the reservoir may be used to draw or help draw infusion medium from the needle. In preferred embodiments, the negative pressure of the reservoir is sufficient to draw medium from the needle into the reservoir, without requiring an additional external force to be applied to the medium. In other embodiments, an external force, such as the force of an hypodermic needle plunger, may be imparted on medium within the needle, to convey or help convey the medium from the needle to the reservoir during a fill or re-fill operation. In either case, the reservoir pressure may be negative relative to the implant environment (the environment within the patient's body, at the implant site), to help reduce the risk of undesired leakage of medium from the reservoir, into the surrounding implant environment.

Fluid exiting the needle 120 enters the volume 126 formed between the valve member 50 and the septum 46. The fluid may then pass through the filter member 54 and into the annular volume 116, between the filter member and the inner wall of the cup member 44. Fluid in the annular volume 116 is then distributed to the apertures 74, through the annular groove 80 and indentations 86 in the cup member 44.

Fluid may be drawn through the apertures 74, for example, by a negative relative pressure within the reservoir housing portion of the infusion device 10 (FIG. 1). Alternatively, or in addition, the outer diameter of the valve member 50 may be made close enough to the inner diameter of the filter member 54 to produce a pressure on fluid within the volume 126 to force the fluid through the apertures 74, after the needle 120 is withdrawn and the spring 52 forces the valve member 50 back toward the septum 46. Other mechanisms may be employed to cause fluid to pass through the apertures 74 and into the reservoir housing portion of the infusion device, including, but not limited to, pressure applied to fluid in the needle by, for example, a syringe plunger.

In this manner, the infusion device 10 (FIG. 1), may be filled or re-filled with a fluid, such as an infusion medium, cleaning medium, testing medium or other medium. In addition, medium may be drawn from the infusion device, through the inlet structure, in a similar manner as described above. However, instead of pressure differentials causing fluid to flow from the needle 120 and out the apertures 74, the pressure differential is set to cause fluid to flow from the reservoir housing portion of the device, through the apertures 74 and into the opening 124 in the needle 120. This may be accomplished, for example, by pulling back on the plunger of a syringe, while the needle 120 holds the valve 50 in the open position shown in FIG. 12.

The distance moved by the valve member 50 between a closed state (FIG. 4) and an open state (FIG. 12) and, thus, the thickness dimension of the volume 126, is designed to allow sufficient fluid flow from the needle opening 124 to the filter member 54. However, in preferred embodiments, the contribution of the volume 126 to the overall thickness T of the inlet structure is minimized. In particular, preferred embodiments of the inlet structure 20 do not require thick volume spaces between the valve member and the septum and, thus may be made relatively thin, without compromising the ability to transfer fluid from (or to) a needle 120.

To function with such preferred embodiments, the needle 120 may be configured with an opening 124 that is relatively close to the tip 128 of the needle, as compared to typical conventional needles. To help exemplify that preferred embodiment of the invention, FIG. 13a shows a needle 120 in accordance with that preferred embodiment, while FIG.

13b shows a typical conventional hypodermic needle 120', which may be employed with other embodiments of the invention.

Figure 13A:
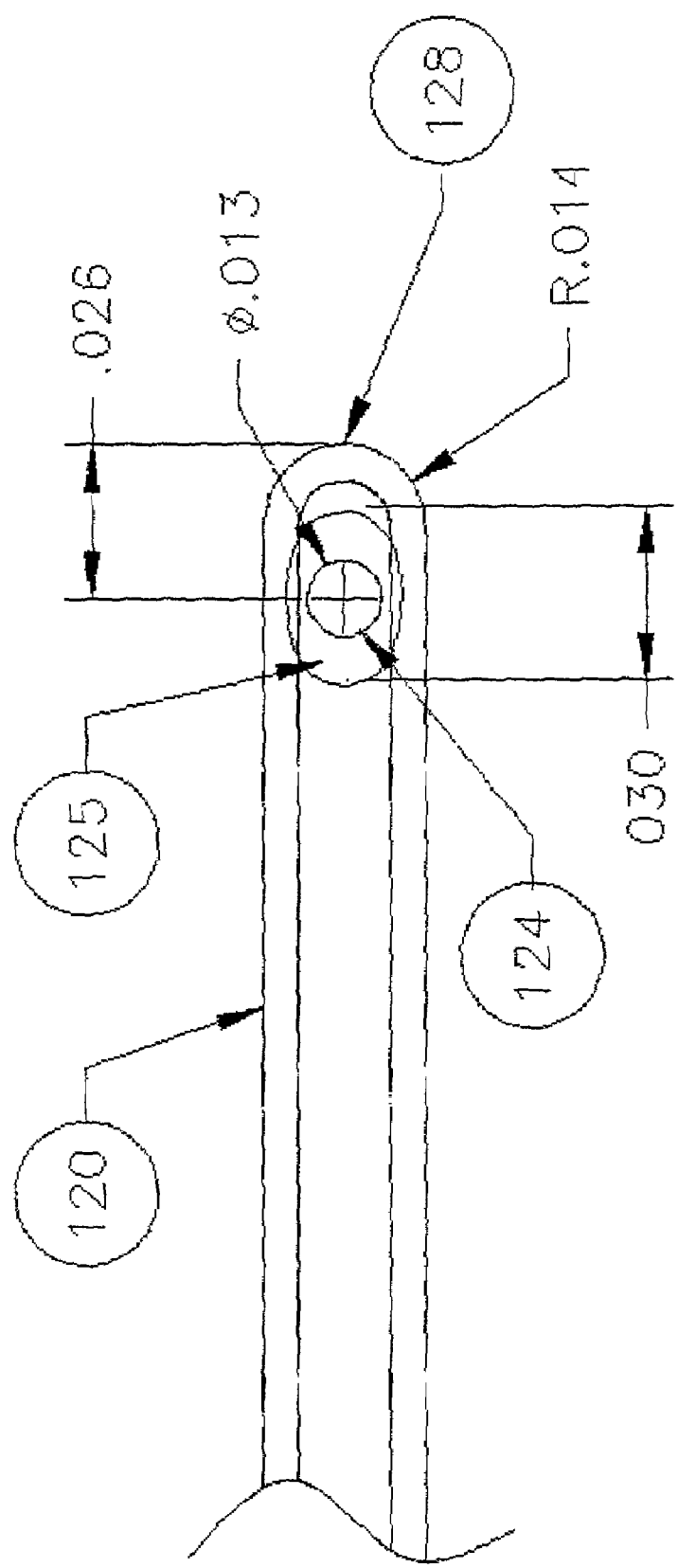
FIG. 13a is a side view of a needle according to an embodiment of the present invention and for use with an inlet structure according to an embodiment of the present invention.

The needle 120 in FIG. 13a includes a needle opening 124 that is located relatively close to the tip 128 of the needle and, preferably, is located at the location at which the needle begins to converge toward the tip 128. In the illustrated embodiment, the needle opening 124 is about 0.025 of an inch (0.064 cm.) from the tip of the needle and has a diameter of about 0.012 of an inch (0.03 cm.). According to one embodiment of the invention, the needle opening 124 may be from 0.025 of an inch to 0.027 of an inch from the tip of the needle and may be in a range from 0.025 of an inch +/−0.020 of an inch. An indentation 125 of a diameter of about 0.026 of an inch (0.066 cm.) may be formed around the opening 124. In preferred embodiments, the indentation abuts or is directly adjacent to the converging portion of the needle tip. In further embodiments, the edge of the indentation 125 is within a distance from the needle tip 128 equal to about one diameter of the needle opening 124 and, more preferably, within a distance of the tip 128 equal to about one half of the diameter of the needle opening 124.

To allow close spacing of the needle opening 124 to the needle tip 128, the radius of the tip of the needle may be made larger than that of typical conventional hypodermic needles. For example, the radius of the needle tip 128 may be within the range of about one quarter to about one half of the diameter of the needle. In the illustrated embodiment, the radius of the needle tip 128 is about 0.014 of an inch (0.036 cm.). The needle may be introduced into the patient through an introducer needle, to reduce trauma to the patient.

Figure 13B:
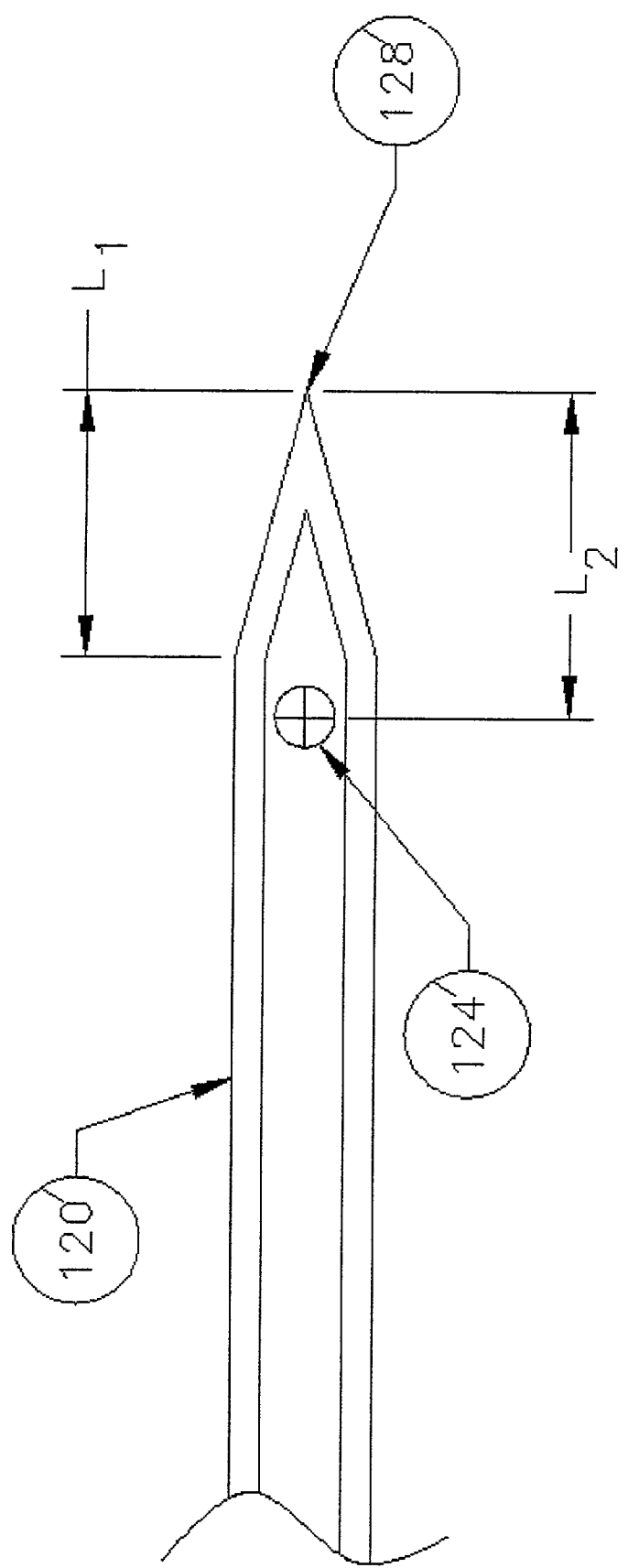
FIG. 13b is a side view of a conventional needle.

In comparison, one example of a typical conventional needle 120' shown in FIG. 13b includes an aperture 124' which is located on the shaft of the needle, well above the location at which the needle converges toward its tip 128'. Conventional hypodermic needles typically include a length $L_1$ devoted solely to converging to the tip 128', requiring the opening 124' to be located at a relatively great distance from the tip 128' as compared to the distance of the opening 124 from the tip 128 of the needle 120 in FIG. 13a. For example, a typical hypodermic needle may have an opening 124' located a distance $L_2$ from the tip 128', where $L_s$ is much greater than $L_1$.

By using a needle 120 having an opening 124 located relatively near the tip 128, such as, but not limited to, the needle shown in FIG. 13a, embodiments of the inlet structure may be configured with a relatively small overall thickness T, to result in a device 10 having a relatively thin form factor. In particular, such embodiments may include a valve member 50 having a depression 110 which is relatively shallow, for example, within the range of about 0.01 inch to about 0.05 inch deep. Because the depression 110 may be made relatively shallow, the thickness $T_V$ of the valve member 50 (FIG. 10), may be relatively small. In this manner, the contribution of the valve member 50 to the overall thickness T of the inlet structure may be minimized or reduced.

In addition, by using a needle 120 having an opening 124 located relatively near the tip 128, such as, but not limited to, the needle shown in FIG. 13a, the distance by which the valve member 50 must be moved to locate the needle opening 124 below the septum and in the volume 126 between the septum and the valve member is relatively small, as compared to a conventional needle as shown in FIG. 13b. In this manner, the inlet structure may be configured to accommodate relatively small strokes or movements of the valve member 50 in the thickness T (or axial A) direction of the device and, thus, may be configured with a relatively small thickness in the space in which the valve member 50 moves. Thus, the contribution of the space between the septum 46 and the open position of the valve member 50 (or between the septum 46 and the end of the cup member 44) to the overall thickness T of the inlet structure 20 may be relatively small, as compared to configurations designed for a conventional needle 120' shown in FIG. 13b.

Therefore, embodiments of the invention relate to an inlet structure for an infusion device, where the inlet structure is configured to operate with a needle having an opening located relatively near the tip (such as, but not limited to, the needle 120 shown in FIG. 13a). Preferred embodiments of the inlet structure are configured with a relatively small thickness in the space in which the valve member 50 moves and, thus, a relatively small overall thickness $T_f$. Further embodiments of the invention relate to a system which includes a needle having an opening located relatively near the tip (such as, but not limited to, the needle 120 shown in FIG. 13a) and an inlet structure of an infusion device, configured to operate with such a needle.

Additional embodiments of the invention relate to infusion devices which include inlet structures as described herein and systems which include needles having an opening located relatively near the tip (such as, but not limited to, the needle 120 shown in FIG. 13a) and infusion devices having inlet structures as described herein. Further embodiments relate to inlet structures (and infusion devices and systems employing inlet structures) that are configured to operate with conventional needles, but include other aspects of the invention described herein. Yet further embodiments relate to methods of making and using the inlet structures, infusion devices and systems described herein.

In the embodiments described above, the septum 46 includes a surface facing the valve member 50 which functions as a valve seat against which the valve member 50 contacts and seals, when in a closed position (as shown in FIG. 4). In preferred embodiments, the septum also functions as a seal, to seal and reseal the opening through which a needle may pass during a fill, refill or fluid withdrawal operation. Another inlet structure embodiment employing a single-piece septum and valve seat is shown in FIG. 14.

Figure 14:
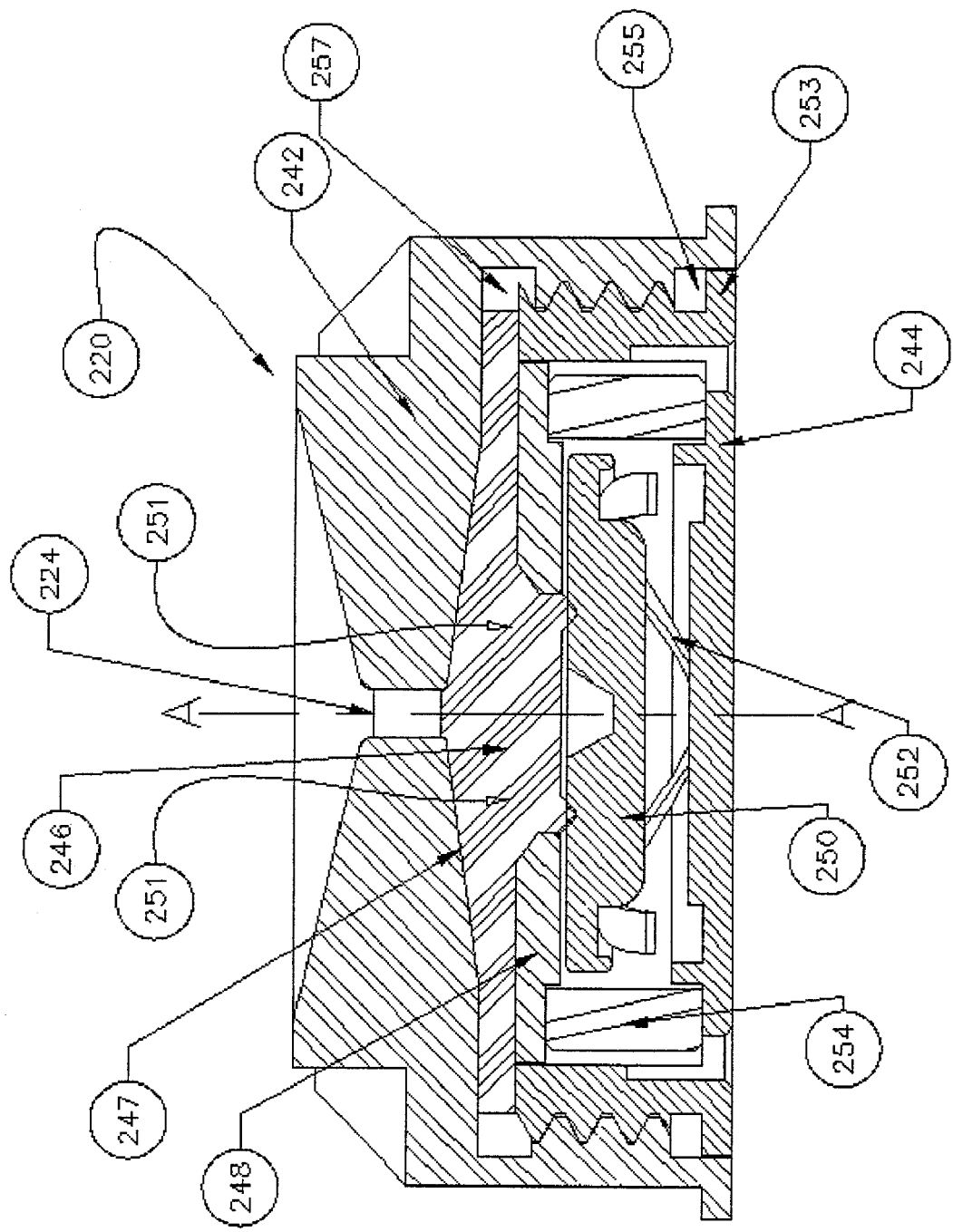
FIG. 14 is a cross-section view of an inlet structure according to another example embodiment of the present invention.
Figure 15:
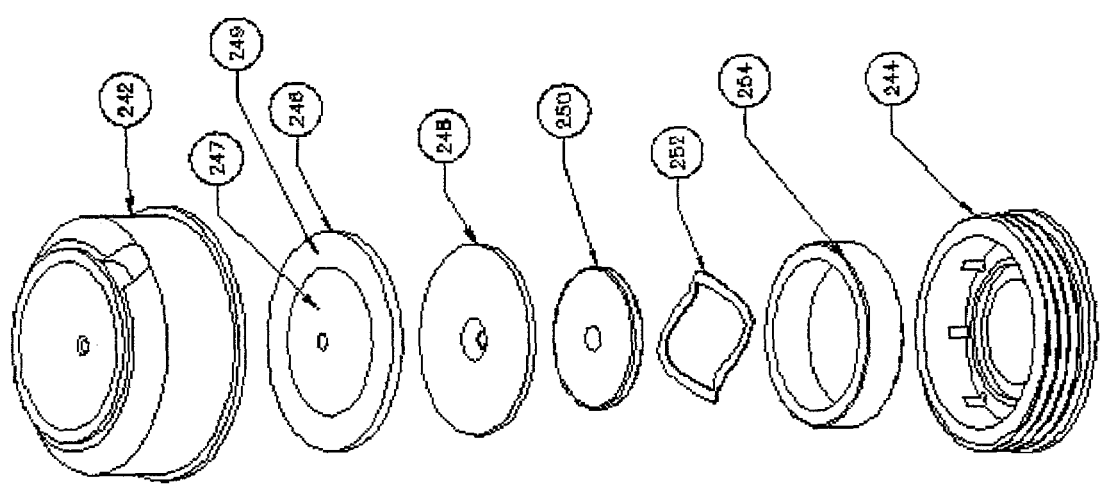
FIG. 15 is an exploded perspective view of the inlet structure of FIG. 14.

In FIG. 14, an inlet structure 220 is configured similarly, in many respects, to the inlet structure 20 of FIG. 4. Components of the inlet structure 220 of FIG. 14 that correspond to similar components in FIG. 4 are labeled with reference numbers that are 200 greater than corresponding components in FIG. 4. Thus, for example, the inlet structure 220 includes an outer cap 242 (corresponding to outer cap 42 in FIG. 4), a cup-shaped member 244 (corresponding to cup-shaped member 44 in FIG. 4), a septum 246 (corresponding to septum 46 in FIG. 4), a support ring 248 (corresponding to ring 48 in FIG. 4), a valve member 250 (corresponding to valve member 50 in FIG. 4), a valve spring 252 (corresponding to spring 52 in FIG. 4), and a filter member 254 (corresponding to filter 54 in FIG. 4). Unless inconsistent with the description and illustrations of the FIG. 14 embodiment, the descriptions of components in the FIG. 4 embodiment are applicable to the corresponding components in FIG. 14. FIG. 15 shows an exploded view of the inlet structure 220 of FIG. 14.

In the embodiment of FIGS. 14 and 15, the septum 246 differs from the septum 46 shown in FIG. 4, in that the septum 246 includes a tapered or generally conical surface 247 facing the closed end of the outer cap 242 and the inlet opening 224. With reference to FIGS. 14 and 15, the tapered surface 247 forms a relatively thick central region of the septum, as compared to the outer peripheral region. In the illustrated embodiment, the conical, tapered surface 247 is centrally located and extends radially outward to a radius less than the outer peripheral radius of the septum, beyond which the septum defines a relatively flat outer peripheral surface 249. The center or apex of the conical, tapered surface is located at the interior end of the inlet opening 224 and may be flattened or provided with a depression to help receive and guide a needle during a needle insertion operation.

As shown in FIG. 14, the septum-facing surface of the outer cap 242 has a centrally located, inwardly conical, tapered depression which matches and engages the tapered surface 247 of the septum. The inlet opening 224 is located at the apex of the conical, tapered depression. The septum-facing surface of the cap 242 also includes an annular, generally flat surface around the conical depression, to engage the generally flat outer peripheral surface 249 of the septum. In this manner, when the cup-shaped member 244 is threadingly coupled to the outer cap 242 and appropriately tightened, the conical, tapered depression surface on the cap 242 engages the conical, tapered surface 247 of the septum 246 at an angle relative to the axis A of the inlet opening 224. As a result, tightening of the outer cap 242 and cup-shaped member 244 results in a force (represented by arrows 251) directed annularly around the inlet opening and angled toward the axis of the inlet opening and, thus toward the path that a needle would take when passed through the inlet opening and through the septum. The force 251 is directed to help close the septum around the shaft of a needle passing through the septum along the inlet axis A. The force 251 may also help close the slit or needle hole left in the septum, for example, after a needle is removed from the septum.

Thus, in the embodiment shown in FIGS. 14 and 15, the conical, tapered surface 247 of the septum 246 and correspondingly tapered depression in the outer cap 242 may be configured to provide a septum sealing force, to help the septum form an effective seal. The generally flat outer surface 249 of the septum 246 may be arranged to engage a corresponding, generally flat annular surface of the outer cap 242, to help center and stabilize the septum 246.

As noted above, the septum 246 includes a valve-facing surface that functions as a valve seat, against which the valve member 250 may engage and seal. Similar to the septum 46 in FIG. 4, the septum 246 may include one or more annular ribs on the valve seat surface (represented by 300 in FIG. 14), for improved sealing capabilities. In the illustrated embodiment, annular ribs are not located on other surfaces of the septum, such as the surfaces 247 and 249, as the engagement of the conical, tapered surfaces may provide sufficient sealing capabilities. In other embodiments, however, one or more annular ribs may be located on surfaces 247 and/or 249 to help improve sealing capabilities, similar to the function of annular rib 96 of septum 46 (of the embodiment of FIGS. 4 and 9).

Also similar to the arrangement shown in FIG. 4, the septum 246 includes an annular recess in which the support ring 248 is disposed. In the FIG. 14 embodiment, the annular recess and support ring are on the opposite surface of the septum 246 with respect to the conical, tapered surface 247. The support ring 248 in the FIG. 14 embodiment functions similarly to the support ring 48 described above with respect to FIG. 4. However, the support ring 248 includes an annular recess at the outer periphery of its valve-facing surface, for receiving a portion of the filter 254. The annular recess helps center and stabilize the components relative to each other.

The outer cap 242 and cup-shaped member 244 in the FIG. 14 embodiment function similarly to the outer cap 42 and cup-shaped member 44 described above with respect to FIG. 4. However, the threaded surfaces of the outer cap 42 and the cup-shaped member 44 do not extend to the bottom (with respect to the orientation shown in FIG. 14) of the inlet structure. Instead, the cup-shaped member 244 is provided with an annular lip 253 extending outward around the closed end of the member 244. A gap 255 is provided between the lip 253 and the threads on the outer surface of the cup-shaped member. The lip 253 and gap 255 provide surfaces that are easier to weld, as compared to a threaded surface. As a result, the cup-shaped member 244 and outer cap 242 may be readily welded together, once the appropriate degree of tightness is achieved by threading the two components together.

In addition, in the embodiment of FIG. 14, the septum is engaged by the open end of the cup-shaped member 244 and is compressed between those two members, upon threadingly tightening the two members together. A gap 257 is provided between the cup-shaped member 244 and the outer cap 242, at the septum-end of the cup-shaped member. Upon threadingly tightening the cup-shaped member 244 and the outer cap 242, the septum 246 is allowed to deform and flow slightly into the gap 257.

Figure 16:
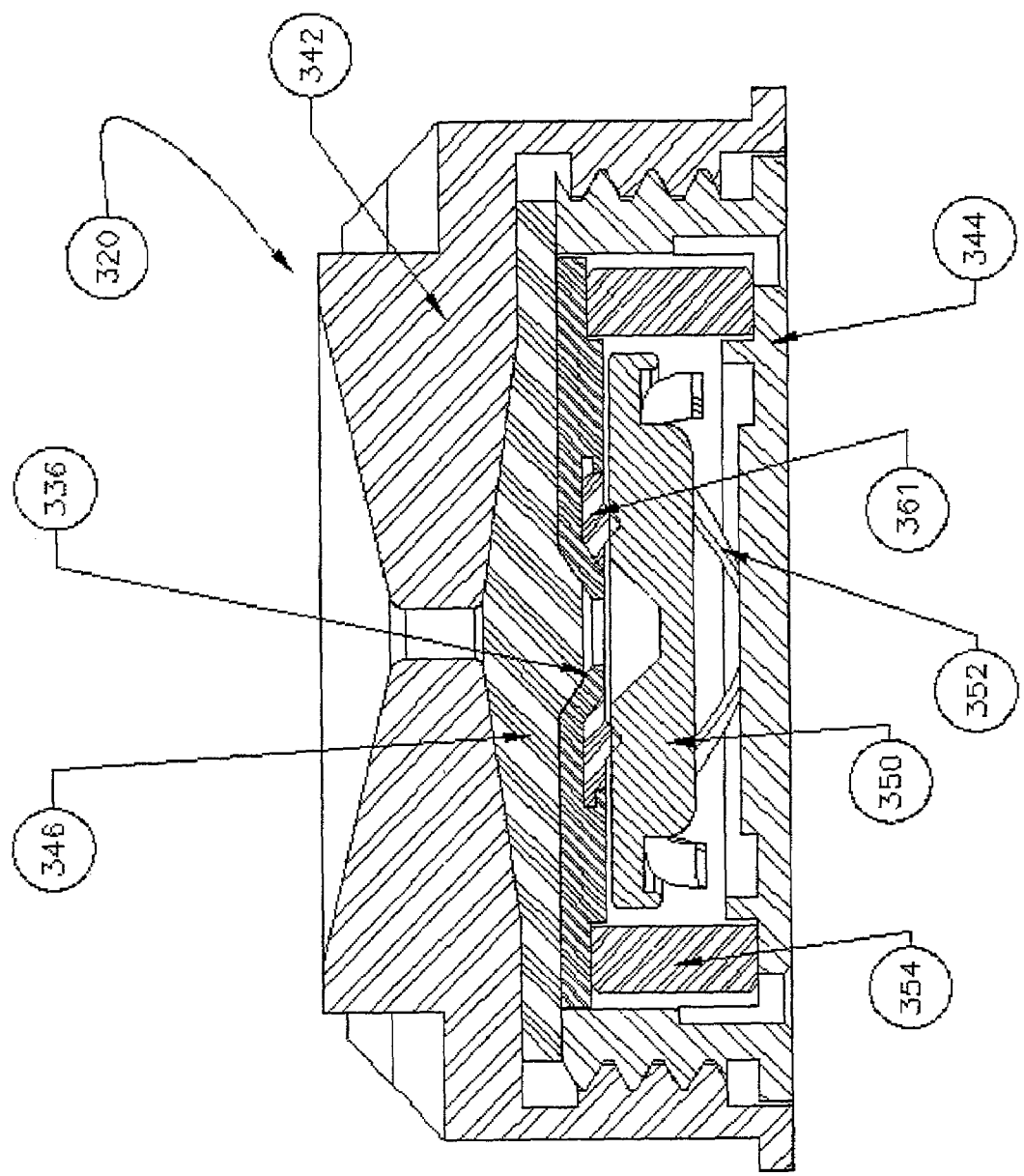
FIG. 16 is a cross-section view of an inlet structure according to yet another example embodiment of the present invention.
Figure 17:
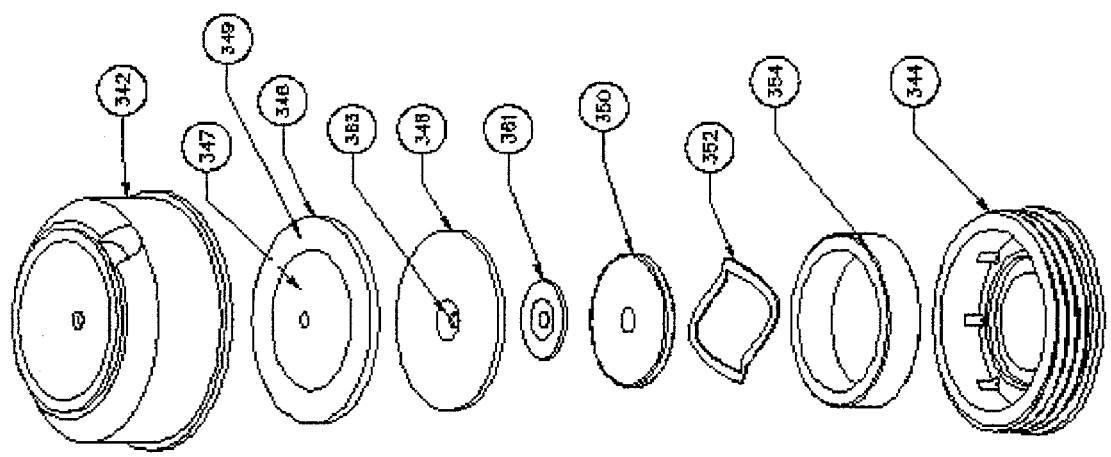
FIG. 17 is an exploded perspective view of the inlet structure of FIG. 16.

Yet another inlet structure embodiment is shown in FIG. 16. In FIG. 16, an inlet structure 320 is configured similarly, in many respects, to the inlet structure 20 of FIG. 4. Components of the inlet structure 320 of FIG. 16 that correspond to similar components in FIG. 4 are labeled with reference numbers that are 300 greater than corresponding components in FIG. 4. Thus, for example, the inlet structure 320 includes an outer cap 342 (corresponding to outer cap 42 in FIG. 4), a cup-shaped member 344 (corresponding to cup-shaped member 44 in FIG. 4), a septum 346 (corresponding to septum 46 in FIG. 4), a support ring 348 (corresponding to ring 48 in FIG. 4), a valve member 350 (corresponding to valve member 50 in FIG. 4), a valve spring 352 (corresponding to spring 52 in FIG. 4), and a filter member 354 (corresponding to filter 54 in FIG. 4). Unless inconsistent with the description and illustrations of the FIG. 16 embodiment, the descriptions of components in the FIG. 4 embodiment are applicable to the corresponding components in FIG. 16. FIG. 17 shows an exploded view of the inlet structure 320 of FIG. 16.

Similar to the embodiment of FIGS. 14 and 15, the embodiment in FIG. 16 includes a septum 346 with a conical, tapered surface 347 and a generally flat outer peripheral surface 349 which face correspondingly shaped surfaces on the outer cap 342. Thus, advantages with respect to improved sealing and stabilization described above with respect to the tapered and generally flat surfaces of the septum and outer cap in FIGS. 14 and 15 are applicable to the corresponding components in FIGS. 16 and 17.

Unlike the embodiment of FIGS. 14 and 15, however, the embodiment of FIGS. 16 and 17 employs a valve seat member 361, separate from the septum 346. The valve seat member 361 may be made of or coated with any suitable infusion medium compatible material such as, but not limited to silicon rubber, ethylane propylene, neoprene, latex, Teflon, or the like. With reference to FIGS. 16 and 17, the valve seat member 361 has a generally circular, disc-shaped body, with a central opening through which a needle may pass. The valve seat member may be disposed in an annular channel provided in the valve-facing surface of the supporting ring 348. In one preferred embodiment, the valve seat member 361 is molded in place in the supporting ring 348.

In other embodiments, other suitable processes of setting the valve seat member 361 in place may be employed.

In the embodiment illustrated in FIGS. 16 and 17, the supporting ring 348 has a smaller central aperture than the supporting rings 248 and 48 shown in embodiments of FIGS. 4 and 14. As a result, the supporting ring 348 has sufficient surface area around the central aperture to provide the annular channel in which the valve seat member 361 is disposed. In a further embodiment, the valve seat may be formed integral with the supporting ring 348, to reduce the number of components in the structure. The septum-facing surface of the supporting ring 348 may be provided with an annular taper 363 around the central aperture, to help guide a needle tip into the central aperture.

Embodiments of the invention may employ any one or combination of aspects described herein for minimizing or reducing the required thickness $T_I$ of the inlet structure, for minimizing or reducing the contribution of the inlet structure to the overall thickness of the infusion device, for improving sealing functions, for improving operational life of the inlet structure and/or for providing other advantages described herein or inherent from the disclosed structures or processes. In one preferred embodiment, all aspects described above are employed to result in an inlet structure or infusion device with a relatively small thickness, including, but not limited to: the selection of a convergence angle of the cone-shaped depression 26 to be within the range of about 60° and 180° and, preferably about 150°; a septum having one or more sealing ribs or a recess for receiving a support ring, to allow the septum to be made relatively thin without compromising sealing or support functions; a cup member having grooves and indentations formed in its inner surfaces, to improve flow of infusion medium without added structural thickness; a septum and cup-member having matching conical, tapered surfaces for improved sealing and stabilization; a valve member having a relatively shallow needle-receiving depression or having a recess for receiving and sharing thickness dimension with a the spring; and an inlet configuration which accommodates a needle having an opening located near its tip and, thus, employs a relatively short stroke of the valve member between closed and open states of the valve member.

Embodiments of the present invention may incorporate septums with no valve. For example, in embodiments where the main seal is provided by the septum, the valve may function as a redundant safety system. Thus, in these embodiments, the valve may be eliminated. As a consequence, there may be a corresponding reduction in the height of the assembly or the septum may be thicker. In addition, embodiments of the present invention may employ multi-layer septums. For example, septums may be arranged in a star-like fashion, each septum being approximately 45° from the next septum.

The foregoing description of preferred embodiments of the invention has been presented for the purposes of illustration and description. It is not intended to be exhaustive or to limit the invention to the precise form disclosed. Many modifications and variations are possible in light of the above teaching. For example, while some embodiments employ drive mechanisms and/or propellants to drive infusion medium out of the reservoir, further embodiments of the infusion device may be configured to deliver or limit delivery of infusion medium by capillary action, diffusion through a membrane or the like, without the requirement of a drive mechanism, control electronics or propellants. In such a configuration, the housing 12 need not include a portion containing a drive mechanism and control electronics. Also, while various embodiments are described above in the context of implantable infusion devices, other embodiments of the invention may employ aspects discussed above in external infusion devices designed to be located external to a patient and connected to the patient through a catheter or the like. Furthermore, while various embodiments described herein include a generally conical-shaped inlet depression to help guide a needle into an inlet opening, other embodiments may include alternative or additional means to help locate an inlet opening and/or guide a needle into the inlet opening. For example, further embodiments may include a ring or other suitable pattern of magnetic material (such as a permanent magnet) disposed around the inlet opening or around the conical inlet depression, where the needle is made of or includes magnetizable material. In other embodiments, the needle may be made of or include a magnetic material for magnetically interacting with magnets or magnetizable material on the inlet structure.

What is claimed is:

1. An infusion device for delivering infusion medium to a patient and for receiving infusion medium from a hollow needle during a fill or re-fill operation, the device comprising:

a housing having a reservoir portion for containing a volume of infusion medium and an outlet through which infusion medium may be dispensed; and an inlet structure provided in fluid flow communication with the reservoir portion of the housing, the inlet structure having an inlet opening, a septum, a moveable valve member and means for imparting a force on the valve member to urge the valve member against the septum;

wherein the septum has a side disposed in relation to the inlet opening, to seal the inlet opening;

wherein the valve member is disposed on the opposite side of the septum relative to the side of the septum that seals the inlet opening, the valve member being moveable between a first state in which the valve member contacts the septum and a second state in which the valve member is spaced from the septum to define a volume space between the septum and the valve member;

wherein the moveable valve member has a first surface for contacting a tip of a needle passed through the inlet opening and the septum to move the valve member to the second state; and wherein upon the valve member being in the second state, the distance between the first surface of the valve member and the septum is no greater than about 0.075 inch.

2. A device as recited in claim 1, the first surface of the moveable valve member having a depression for receiving a tip of a needle passed through the inlet opening and the septum, the depression in the first surface of the valve member having a depth within the range of about 0.01 inch and about 0.05 inch.

3. A device as recited in claim 2, wherein the depression in the first surface of the valve member has a depth of no more than about 0.03 inch.

4. An infusion device for delivering infusion medium to a patient and for receiving infusion medium from a hollow needle during a fill or re-fill operation, the device comprising:

a housing having a reservoir portion for containing a volume of infusion medium and an outlet through which infusion medium may be dispensed; and an inlet structure provided in fluid flow communication with the reservoir portion of the housing, the inlet structure having an inlet opening, a septum, a moveable valve member moveable between a first state and a second state, and means for imparting a force on the valve member to urge the valve member toward the first state;

wherein the moveable valve member has a first surface for contacting the septum when the valve member is in the first state, and wherein the septum includes at least one rib disposed to contact the first surface of the valve member upon the valve member being in the first state, for improving a seal between the septum and the valve member upon the valve member being in the first state.

5. A device as recited in claim 4, wherein the at least one rib comprises an annular rib.

6. A device as recited in claim 4, wherein:
the inlet structure further comprises a cup-shaped member in which the septum, the moveable valve member and the means for imparting a force are disposed;
the septum includes at least one second rib contacting the cup-shaped member for improving a seal between the septum and the cup-shaped member.

7. A device as recited in claim 6, wherein the septum comprises a generally disc-shaped member having an outer peripheral edge and wherein the at least one second rib comprises a peripheral rib disposed around the outer peripheral edge of the generally disc-shaped member.

8. A device as recited in claim 6, wherein the inlet structure further includes a cap member having an inner surface disposed adjacent the septum and wherein the septum includes at least one third rib contacting the inner surface of the cap member for improving a seal between the septum and the cap member.

9. A device as recited in claim 8, wherein the septum includes a central portion disposed adjacent the inlet opening to seal the inlet opening and wherein the at least one third rib comprises an annular rib surrounding the central portion of the septum.

10. A device as recited in claim 4, wherein the inlet structure further includes a cap member having an inner surface disposed adjacent the septum and wherein the septum includes at least one further rib contacting the cap member for improving a seal between the septum and the cap member.

11. A device as recited in claim 10, wherein the septum includes a central portion disposed adjacent the inlet opening to seal the inlet opening and wherein the at least one further rib comprises an annular rib surrounding the central portion of the septum.

12. A system for filling or re-filling an infusion device, comprising:
a generally hollow needle having a generally hollow interior, a needle shaft terminating in a tip end and an opening on the needle shaft in fluid flow communication with the interior of the needle, the needle further having a converging portion between the needle shaft and the needle tip, wherein the distance between the needle tip and the needle opening is within the range of about 0.01 inch and about 0.05 inch;

an infusion device housing having a reservoir portion for containing a volume of infusion medium and an outlet through which infusion medium may be dispensed; and an inlet structure provided in fluid flow communication with the reservoir portion of the housing, the inlet structure including an inlet opening, a septum having a first side disposed in relation to the inlet opening to seal the inlet opening, and a moveable valve member disposed on the opposite side of the septum relative to the first side of the septum, the valve member being moveable between two maximum end points of movement respectively defining a first state in which the valve member is adjacent the septum and a second state in which the valve member is spaced from the septum relative to the first state to define a volume space between the septum and the valve member;

wherein the inlet opening has a dimension large enough to allow the needle to pass through the inlet opening and through the septum to contact and move the moveable valve member;

wherein the moveable valve member has a first surface for contacting the a tip of a needle passed through the inlet opening and the septum to receive a force from the needle to move the valve member to the second state, wherein upon the valve member being in the second state, the distance between the first surface of the valve member and the septum is no greater than about 0.05 inch.

13. A system as recited in claim 12, wherein the moveable valve member has a first surface for contacting the septum when the valve member is in the first state, the first surface of the moveable valve member having a depression for receiving a tip of a needle passed through the inlet opening and the septum, the depression in the first surface of the valve member having a depth within the range of about 0.01 inch and about 0.05 inch.

14. A system as recited in claim 12, wherein the distance between the needle tip and the center of the needle opening is about 0.025 inch.

* * * * *